(12) United States Patent
Nichter et al.

(10) Patent No.: US 8,636,656 B2
(45) Date of Patent: Jan. 28, 2014

(54) RETRACTOR ASSEMBLIES WITH BLADE DRIVE MECHANISMS

(75) Inventors: Paula A. Nichter, Memphis, TN (US); Paul F. Wheeler, Hemando, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 227 days.

(21) Appl. No.: 13/210,842

(22) Filed: Aug. 16, 2011

(65) Prior Publication Data

US 2013/0046147 A1  Feb. 21, 2013

(51) Int. Cl.
*A61B 1/32* (2006.01)

(52) U.S. Cl.
USPC .................. 600/228; 600/225; 600/222

(58) Field of Classification Search
USPC ......... 600/228, 201, 204, 208, 213, 214, 215, 600/219, 221, 222, 225, 226, 227, 229, 231, 600/233, 235
See application file for complete search history.

(56) References Cited

U.S. PATENT DOCUMENTS

| | | |
|---|---|---|
| 563,236 A | 6/1896 | Penhall |
| 1,400,616 A | 12/1921 | McCrory |
| 1,613,141 A | 1/1927 | Stain |
| 2,661,735 A | 12/1953 | Darden |
| 2,670,731 A | 3/1954 | Zoll et al. |
| 2,693,795 A | 11/1954 | Grieshaber |
| 3,054,398 A | 9/1962 | Kobler |
| 3,747,592 A | 7/1973 | Santos |
| 3,752,149 A | 8/1973 | Ungar et al. |
| 3,788,318 A | 1/1974 | Kim et al. |
| 3,965,890 A | 6/1976 | Gauthier |
| 4,263,899 A | 4/1981 | Burgin |
| 4,380,999 A | 4/1983 | Healy |
| 4,545,374 A | 10/1985 | Jacobson |
| 4,716,901 A | 1/1988 | Jackson et al. |
| 4,747,394 A | 5/1988 | Watanabe |
| 4,765,311 A | 8/1988 | Kulik et al. |
| 4,817,587 A | 4/1989 | Janese |
| 4,852,552 A | 8/1989 | Chaux |
| 4,862,891 A | 9/1989 | Smith |
| 4,899,729 A | 2/1990 | Gill et al. |
| 5,027,793 A | 7/1991 | Engelhardt et al. |
| 5,052,373 A | 10/1991 | Michelson |
| 5,125,396 A | 6/1992 | Ray |
| 5,139,511 A | 8/1992 | Gill et al. |
| 5,158,545 A | 10/1992 | Trudell et al. |
| 5,163,949 A | 11/1992 | Bonutti |
| 5,197,971 A | 3/1993 | Bonutti |

(Continued)

FOREIGN PATENT DOCUMENTS

| | | |
|---|---|---|
| DE | 87 04 901 U | 9/1987 |
| EP | 0 856 286 | 8/1998 |

(Continued)

*Primary Examiner* — Todd Manahan
*Assistant Examiner* — Marcela I Shirsat
(74) *Attorney, Agent, or Firm* — Sorell Lenna & Schmidt LLP

(57) ABSTRACT

A retractor assembly for surgery in a patient includes at least one retractor member removably engageable to a support member. The retractor assembly includes a housing assembly engaged to the support member and to an arm that extends from a retraction portion of the retractor member. A drive mechanism in the housing assembly is coupled to the retractor member and is operable to rotate the retraction portion of the retractor member relative to the support member to a desired angular orientation.

22 Claims, 15 Drawing Sheets

(56) References Cited

U.S. PATENT DOCUMENTS

| | | |
|---|---|---|
| 5,299,563 A | 4/1994 | Seton |
| 5,312,417 A | 5/1994 | Wilk |
| 5,339,803 A | 8/1994 | Mayzels et al. |
| 5,353,784 A | 10/1994 | Nady-Mohamed |
| 5,375,481 A * | 12/1994 | Cabrera et al. ............ 74/577 M |
| 5,389,080 A | 2/1995 | Yoon |
| 5,490,819 A | 2/1996 | Nicholas et al. |
| 5,503,617 A | 4/1996 | Jako |
| 5,509,893 A | 4/1996 | Pracas |
| 5,512,038 A | 4/1996 | O'Neal et al. |
| 5,549,595 A | 8/1996 | Freitas |
| 5,573,517 A | 11/1996 | Bonutti et al. |
| 5,618,260 A | 4/1997 | Caspar et al. |
| 5,667,481 A | 9/1997 | Villalta et al. |
| 5,674,240 A | 10/1997 | Bonutti et al. |
| 5,681,265 A | 10/1997 | Maeda et al. |
| 5,688,223 A | 11/1997 | Rosendahl |
| 5,707,359 A | 1/1998 | Bufalini |
| 5,728,046 A | 3/1998 | Mayer et al. |
| 5,755,732 A | 5/1998 | Green et al. |
| 5,776,054 A | 7/1998 | Bobra |
| 5,779,629 A | 7/1998 | Hohlen |
| 5,785,648 A | 7/1998 | Min |
| 5,795,291 A | 8/1998 | Koros |
| 5,813,978 A | 9/1998 | Jako |
| 5,823,947 A | 10/1998 | Yoon et al. |
| 5,865,731 A | 2/1999 | Lenox et al. |
| 5,888,196 A | 3/1999 | Bonutti |
| 5,928,139 A | 7/1999 | Koros et al. |
| 5,931,777 A | 8/1999 | Sava |
| 5,944,658 A | 8/1999 | Koros et al. |
| 5,951,466 A | 9/1999 | Segermark et al. |
| 5,961,499 A | 10/1999 | Bonutti et al. |
| 5,976,146 A | 11/1999 | Ogawa et al. |
| 6,027,518 A | 2/2000 | Gaber |
| 6,042,540 A | 3/2000 | Johnston et al. |
| 6,074,343 A | 6/2000 | Nathanson et al. |
| 6,074,380 A | 6/2000 | Byrne et al. |
| 6,083,154 A | 7/2000 | Liu et al. |
| 6,096,046 A | 8/2000 | Weiss et al. |
| 6,099,547 A | 8/2000 | Gellman et al. |
| 6,139,493 A | 10/2000 | Koros et al. |
| 6,149,583 A | 11/2000 | Vierra et al. |
| 6,162,236 A | 12/2000 | Osada |
| 6,171,299 B1 | 1/2001 | Bonutti |
| 6,187,000 B1 | 2/2001 | Davison et al. |
| 6,196,969 B1 | 3/2001 | Bester et al. |
| 6,200,322 B1 | 3/2001 | Branch et al. |
| 6,224,545 B1 | 5/2001 | Cocchia et al. |
| 6,296,609 B1 | 10/2001 | Brau |
| 6,312,443 B1 | 11/2001 | Stone |
| 6,325,812 B1 | 12/2001 | Dubrul et al. |
| 6,361,492 B1 | 3/2002 | Santilli |
| 6,371,911 B1 | 4/2002 | Hossain et al. |
| 6,394,950 B1 | 5/2002 | Weiss |
| 6,431,025 B1 | 8/2002 | Koros et al. |
| 6,450,952 B1 | 9/2002 | Rioux et al. |
| 6,602,189 B1 | 8/2003 | Bennetti et al. |
| 6,616,605 B2 | 9/2003 | Wright |
| 6,749,563 B2 | 6/2004 | Stihl |
| 6,945,933 B2 | 9/2005 | Branch |
| 7,473,223 B2 * | 1/2009 | Fetzer ............. 600/213 |
| 8,062,217 B2 * | 11/2011 | Boucher et al. ............. 600/215 |
| 2003/0055319 A1 | 3/2003 | Chang |
| 2004/0002629 A1 | 1/2004 | Branch et al. |
| 2004/0176665 A1 | 9/2004 | Branch et al. |
| 2004/0230191 A1 | 11/2004 | Frey et al. |
| 2005/0113644 A1 | 5/2005 | Obenchain et al. |
| 2005/0192485 A1 | 9/2005 | Branch et al. |
| 2005/0234304 A1 | 10/2005 | Dewey et al. |
| 2006/0069315 A1 | 3/2006 | Miles et al. |
| 2007/0156024 A1 * | 7/2007 | Frasier et al. ............. 600/219 |
| 2008/0114208 A1 * | 5/2008 | Hutton et al. ............. 600/201 |
| 2009/0036746 A1 * | 2/2009 | Blackwell et al. ............ 600/219 |

FOREIGN PATENT DOCUMENTS

| | | |
|---|---|---|
| EP | 0 951 868 | 10/1999 |
| EP | 1 053 717 A1 | 11/2000 |
| EP | 1 192 905 | 9/2001 |
| FR | 1 019 217 A | 1/1952 |
| FR | 2 788 958 | 8/2000 |
| FR | 2 807 313 | 10/2001 |
| WO | WO 2005/030318 | 4/2005 |
| WO | WO 2011/112878 A1 * | 9/2011 ............. A61B 1/32 |

* cited by examiner

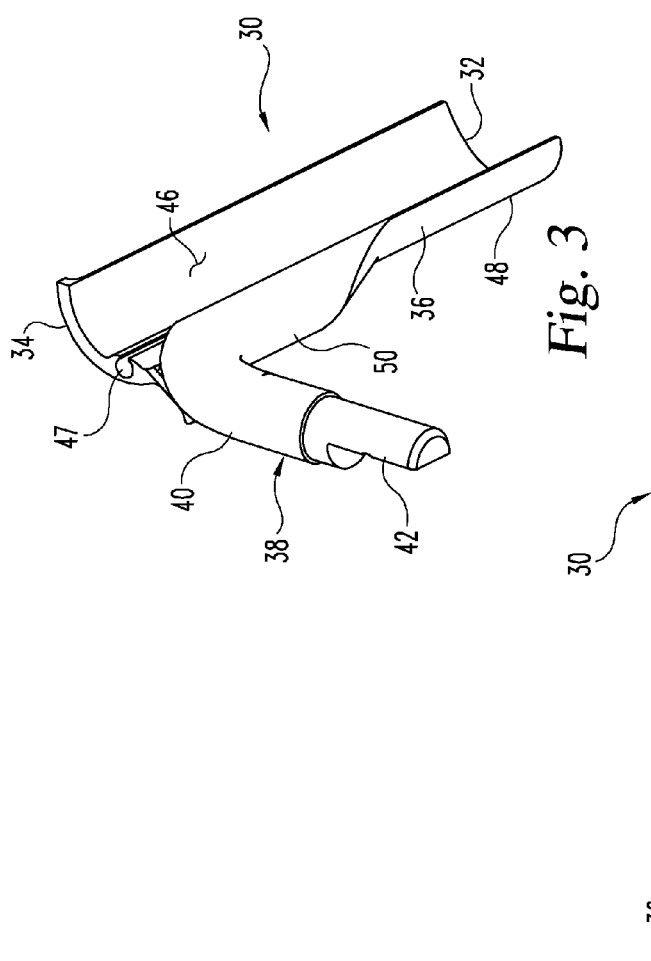
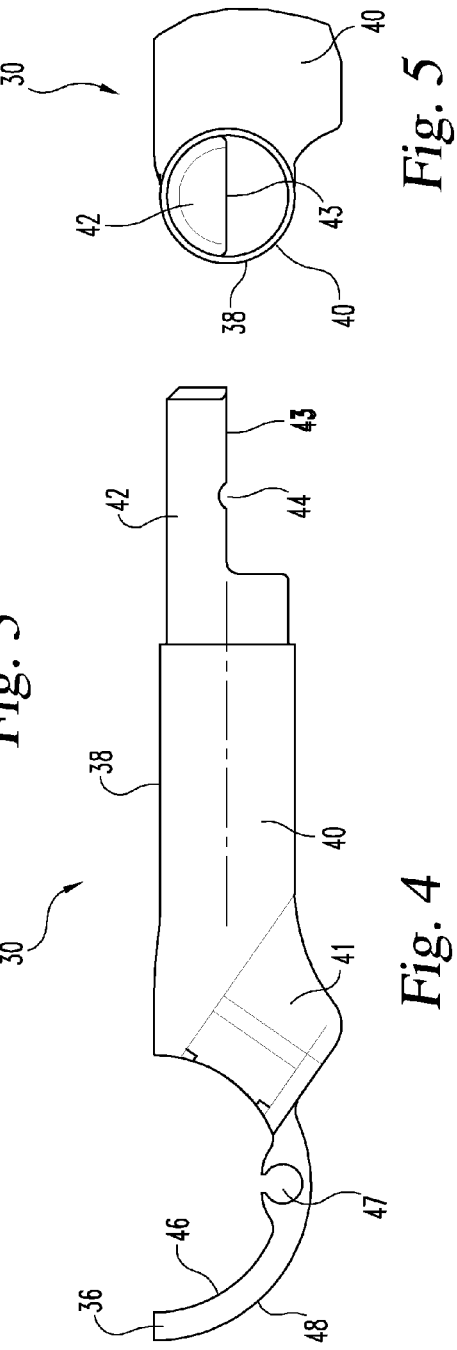

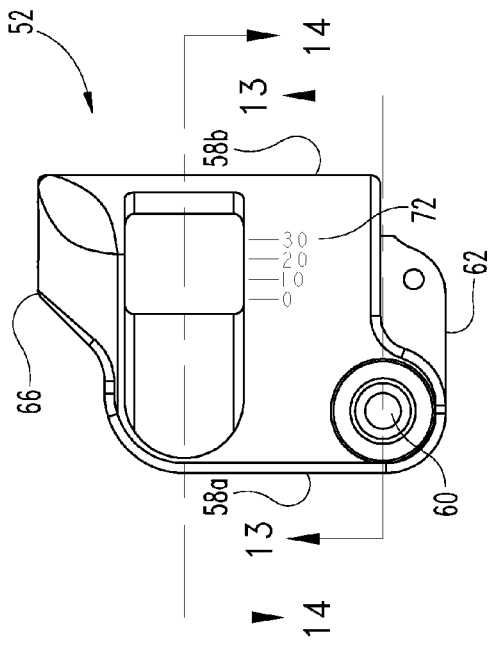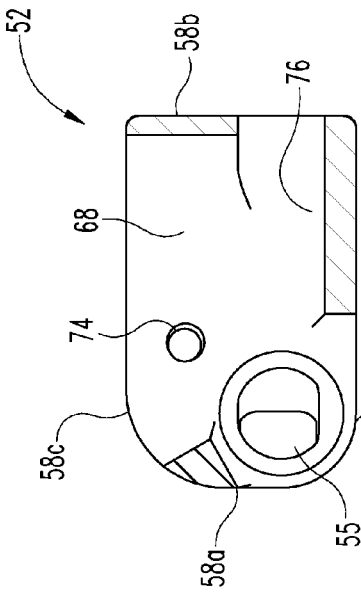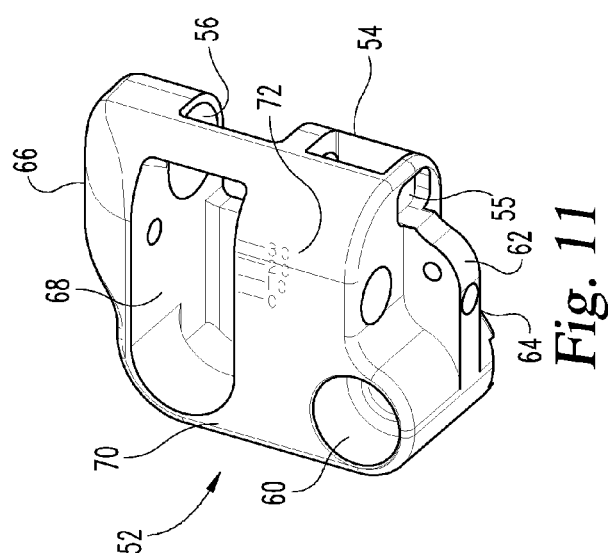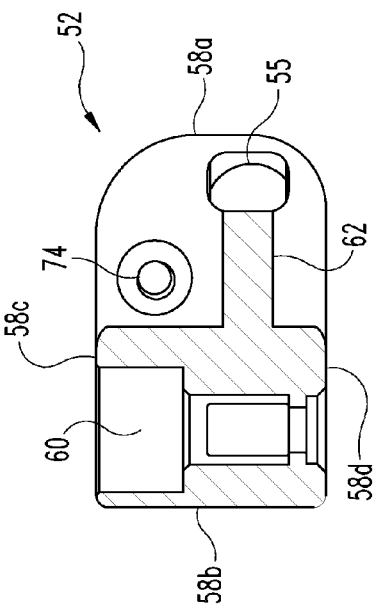

RETRACTOR ASSEMBLIES WITH BLADE DRIVE MECHANISMS

BACKGROUND

The present application relates to retractor assemblies and methods for use in performing surgery in a patient, and more particularly, but not exclusively, relates to assemblies for tissue retraction to facilitate a procedure within a patient through the retracted tissue.

Traditional surgical procedures for pathologies located within the body can cause significant trauma to the intervening tissues. These procedures often require a long incision, extensive muscle stripping, prolonged retraction of tissues, denervation and devascularization of tissue. These procedures can require operating room time of several hours and several weeks of post-operative recovery time due to the destruction of tissue during the surgical procedure. In some cases, these invasive procedures lead to permanent scarring and pain that can be more severe than the pain leading to the surgical intervention.

The development of minimally invasive surgical procedures and instruments has yielded a major improvement in reducing recovery time and post-operative pain because minimal dissection of tissue, such as muscle tissue, is required. For example, minimally invasive surgical techniques are desirable for spinal and neurosurgical applications because of the need for access to locations within the body and the danger of damage to vital intervening tissues. While developments in surgical procedures and instruments have provided steps in the right direction, there remains a need for further development in tissue retraction devices and methods.

SUMMARY

One nonlimiting embodiment of the present application is directed to a retractor assembly for surgery in a patient that includes at least one retractor member movably engageable to a support member. The retractor assembly includes a housing assembly that is engaged to the support member and also is engaged to an arm extending from a retraction portion of the retractor member. A drive mechanism in the housing assembly is coupled to the retractor member and is operable to pivot the retraction portion of the retractor member relative to the support member to a desired angle. The housing assembly can include a biasing member to bias the retractor member from a pivoted position toward a neutral position. The housing assembly may also include a translation mechanism to move the retractor member linearly along the support member, a lever mechanism to releasably lock the retractor member in a selected position along the support member, and a locking mechanism to releasably lock the retractor member to the housing assembly.

In one form of the embodiment, the drive mechanism is configured to allow infinitely small adjustments in the angulation of the retractor member. The drive mechanism can also be recessed in or flush relative to the housing so that no components project from the housing to interfere with the surgeon and instruments during surgery. In another form, the housing includes a receiving opening facing the side of the surgical approach into the patient so that the arm of the retractor member is positionable in an end-wise manner through the side opening to engage the locking mechanism, making engagement of the retractor member easier than if the retractor member were positioned in a proximal or distal facing opening of the housing. In yet another form, the retractor assembly includes a second retractor member facing the retractor member. At least one of the retractor members may be linearly movably toward and away from the other retractor member. The at least one retractor member is pivotal relative to the other retractor member to move a distal end of the at least one retractor member toward and away from the distal end of the other retractor member.

Another embodiment of the present application is a unique system for surgery in a patient. Other embodiments include unique methods, systems, devices, kits, assemblies, equipment, and/or apparatus involving a retractor assembly.

Further embodiments, forms, features, aspects, benefits, objects and advantages of the present application shall become apparent from the detailed description and figures provided herewith.

BRIEF DESCRIPTION OF THE FIGURES

FIG. 3 is a perspective view of a retractor member of the retractor assembly.

FIG. 4 is a top plan view of the retractor member of FIG. 3.

FIG. 5 is an elevation view of an arm of the retractor member of FIG. 3.

FIG. 11 is a perspective view of a housing body comprising a portion of the housing assembly of FIG. 6.

FIG. 12 is a proximal plan view of the housing of FIG. 11.

FIG. 13 is a section view of the housing along line 13-13 of FIG. 12.

FIG. 14 is a section view of the housing along line 14-14 of FIG. 12.

DESCRIPTION OF THE ILLUSTRATED EMBODIMENTS

Figure 1:
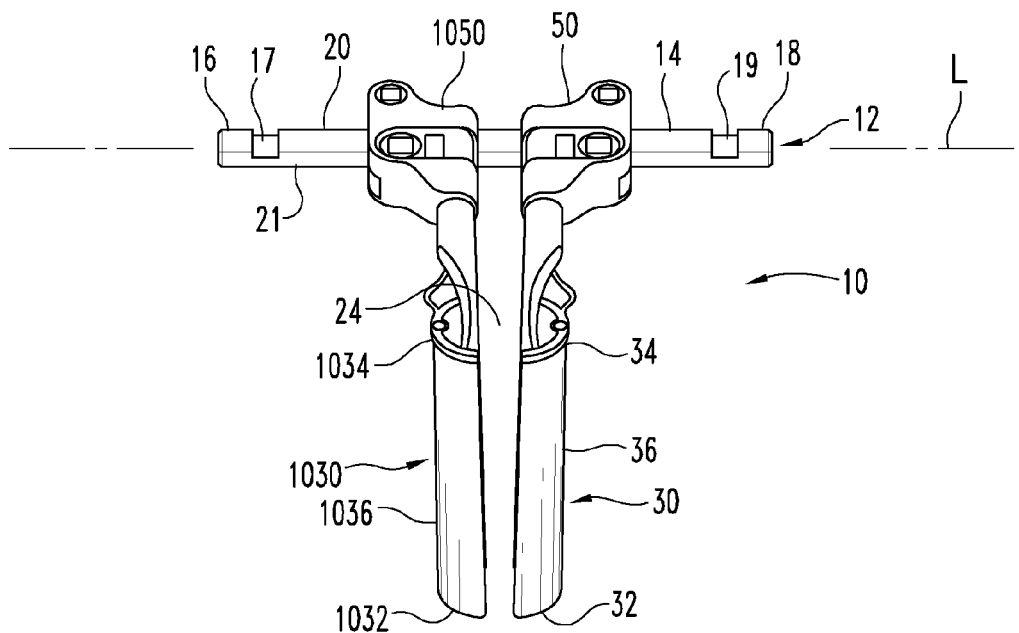
FIG. 1 is perspective view of a retractor assembly for tissue retraction surgery in a patient.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices and described methods, and any such further applications of the principles of the invention as illustrated herein are contemplated as would normally occur to one skilled in the art to which the invention relates.

Instruments, assemblies and methods for performing surgery, including spinal surgeries that include one or more techniques such as laminotomy, laminectomy, foramenotomy, facetectomy, discectomy, interbody fusion, spinal nucleus or disc replacement, and implant insertion including plates, rods, and bone engaging fasteners, for example, are provided. The surgery is performed through a working channel or passageway through skin and/or tissue of the patient provided by a retractor assembly which includes at least one retractor member. Viewing of the surgical site at the working end of the retractor member can be accomplished with naked eye visualization, microscopic viewing devices, loupes, viewing instruments mounted on the retractor member, positioned over the retractor member, positioned in other portals in the body, and/or through a viewing system such as lateral fluoroscopy. The retractor member is movable in situ to increase the size of the working channel to facilitate access to the working space at the distal end of the retractor member while minimizing trauma to tissue surrounding the retractor member. The retractor member can be used with any surgical approach to the spine, including anterior, posterior, posterior mid-line, lateral, postero-lateral, and/or antero-lateral approaches, and in other regions besides the spine.

Referring now generally to FIG. 1, there is illustrated in perspective view one embodiment retractor assembly 10. Assembly 10 includes an elongate support member 12 including an elongate body 14 extending along a longitudinal axis L between a first end 16 and an opposite second end 18. First end 16 and second end 18 are generally structured to engage with one or more operating room support structures (not shown). More particularly, first end 16 and second end 18 each include a notch 17, 19, respectively, configured to receive a corresponding fastening member (not shown) from the operating room support structure. Examples of operating room support structures include, without limitation, support arms, braces and other linkage members which are coupled to an operating table or bed and movable to position retractor assembly 10 relative to a surgical site of the patient. Elongate support member 12 also includes a plurality of teeth (not shown) positioned on outer facing surface 20 thereof. As used herein, an "outer" facing or oriented structure of retractor assembly 10 is oriented away from the retracting members forming the operating portal, while an "inner" surface 21, member, or other feature of retractor assembly 10 is oriented toward the retracting members forming operating portal. In other embodiments of support member 12, other surface features on outer surface 20 or any other facing surface can be provided, such as serrations, knurling, notches, grooves, indentations, projections and/or polymeric, ceramic or metallic coatings, could be provided on one or more surfaces of support member 12 in addition to or in lieu of teeth. Still, in other embodiments, it is contemplated that support member 12 is free from any surface features. In still other embodiments, support member 12 is not elongated and/or longitudinal, but could be provided in the form of a ring, C-shaped member, or other suitable shape.

Figure 2:
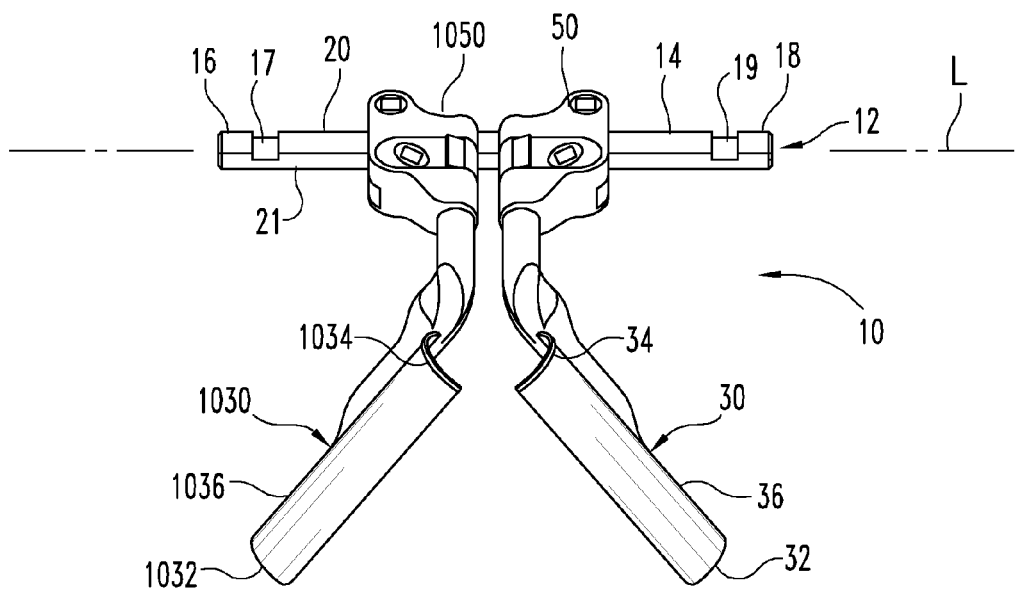
FIG. 2 is a perspective view of the retractor assembly of FIG. 1 with retractor members thereof in a pivoted orientation.
Figure 7:
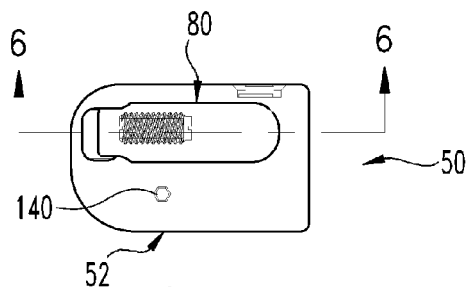
FIG. 7 is a side elevation view looking toward the outer side of the housing assembly of FIG. 6.
Figure 6:
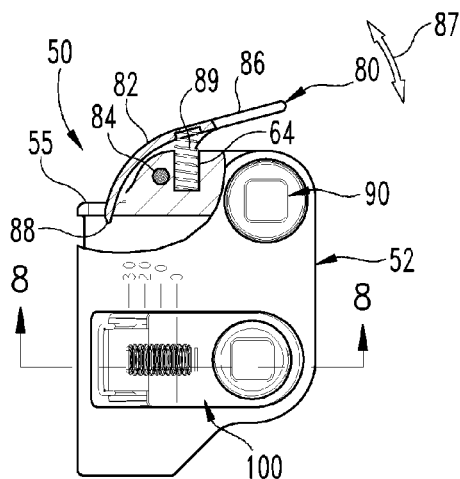
FIG. 6 is a plan view, in partial section along line 6-6 of FIG. 7, of a proximal side of a housing assembly of the retractor assembly.
Figure 9:
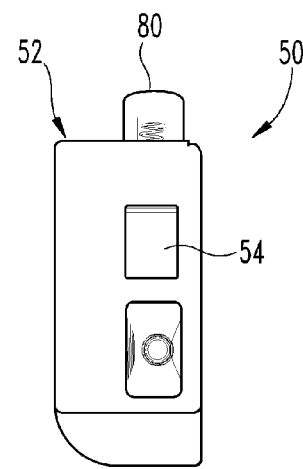
FIG. 9 is a right side elevation view of the housing assembly of FIG. 6.

Retractor assembly 10 includes a first retractor member 30 and a second retractor member 1030. First and second retractor members 30, 1030 are removably engageable to and movable along elongate support member 12, further details of which will be provided below. First and second retractor members 30, 1030 are movable from a first orientation in which retractor members 30, 1030 are perpendicular or substantially perpendicular to support member 12 and its longitudinal axis L, as shown in FIG. 1, to a second orientation where retractor members 30, 1030 are substantially non-perpendicular to support member 12 and its longitudinal axis L, as show in FIG. 2. In the second orientation, distal ends 32, 1032 of retractor members 30, 1030 are pivoted away from one another to expand the size of the working channel 24 between retractor members 30, 1030, particularly at distal ends 32, 1032, facilitating access to and increasing the size of the working space at and distally of distal ends 32, 1032 to provide addition room for manipulating instruments and implants at the surgical site by the surgeon.

In addition, retractor members 30, 1030 are translatable along support member 12 in a direction paralleling longitudinal axis L to move the entire retractor member 30, 1030 toward and away from the other from a first position where facing adjacent longitudinal edges of retractor members 30, 1030 contact one another from proximal ends 34, 1034 to distal ends 32, 1032 to a second position where the facing adjacent longitudinal edges are spaced from one another from proximal ends 34, 1034 to distal ends 32, 1032. In the illustrated embodiment, in the first position retractor members 30, 1030 define and completely encircle or enclose working channel 24, and in the second position the working channel is defined by retraction portions 36, 1036 of retractor members 30, 1030 and the skin and tissue of the patient extending between the separated longitudinal edges of retractor members 30, 1030. In the illustrated embodiment, retractor member 1030 and the housing assembly 1050 connecting it to support member 12 are minor images of but otherwise identical to retractor member 30 and its housing assembly 50. Other embodiments contemplate that retractor member 1030 and/or housing assembly 1050 differ from retractor member 30 and housing assembly 50. In addition, other embodiments contemplate one of the retractor members, such as retractor member 1030, may be non-translatable and/or non-pivotal relative to support member 12. In still other embodiments, retractor members 30, 1030 could be incorporated as one piece with their respective housing assembly 50, 1050 so that retractor members 30, 1030 are integral and non-removable from the respective housing assembly 50, 1050. In another embodiment, retractor members 30, 1030 are simultaneously engaged to or integrally incorporated into a single housing assembly.

Further details of first retractor member 30 will now be discussed with reference to FIGS. 3-5, it being understood that retractor member 1030 can be, but is not required to be, identical to retractor member 30 and thus will not be separately described in detail herein. As discussed above, retractor member 30 includes a retraction portion 36 extending from distal end 32 to proximal end 34. Retractor member 30 includes an elongated arm 38 extending laterally from proximal end 34 for engagement with housing assembly 50, as discussed further below. Arm 38 includes an enlarged transition portion 40 integrally formed with retraction portion 36 to provide a stable platform for transmission of pivoting and translation forces to retraction portion 36 to manipulate and hold back the patient's tissue. Arm 38 also includes a connection portion 42 that is received in housing assembly 50 to couple retractor member 30 to support member 12. Connection portion 42 is smaller in cross-section than transition portion 40 so that connection portion 42 fits in housing assembly 50. Connection portion 42 includes a semi-circular shape with a flat side 43. In addition, connection portion 42 includes a mounting feature 44 on flat side 43 thereof that allows retractor member 30 to be locked to housing assembly 50, as discuss in further detail below. In the illustrated embodiment, mounting feature 44 is a semi-circular recess or groove that extends across flat side 43.

Retraction portion 36 includes a semi-circular cross-section extending from distal end 32 to proximal end 34. The cross-section is defined by a concave inner surface 46 and an opposite convex outer surface 48. Outer surface 48 abuts and retracts tissue of the patient, while inner surface 46 defines a portion of working channel 24 extending from and opening at proximal end 34. Retraction portion 36 may have a fixed length, shape and cross-section, or may include any one or combination of adjustable length, shape, or cross-section. Inner surface 46 also defines and substantially encloses a passage 47 that opens at proximal end 34 and extends along inner surface 46 to a distal opening at or proximally of distal end 32. Passage 47 receives a stability pin (not shown) to dock retractor member 30 to a bony structure. In the illustrated embodiment, passage 47 is not enclosed, but is open along the inner side of passage 47 so that the stability pin is not completely enclosed. In other embodiments, passage 47 can receive light fixtures, tubes for irrigation and suction, or other instruments to be positioned in working channel 24. In addition, transition portion 41 and proximal end 34 define at their junction a valley 49 for receiving and retaining instruments to be positioned into working channel 24 and that are supported by the proximal end of retractor member 30. In one embodiment, valley 49 receives and holds a light source in working channel 24.

In the illustrated embodiment, arm 38 extends substantially orthogonally to retraction portion 36 and is located slightly proximally of proximal end 34 of retraction portion 36. However, in other non-illustrated embodiments, it is contemplated that arm 38 could be angled relative to retraction portion 36, or located at or distally of proximal end 34. In addition, retraction portion 36 can include cross-sectional shapes other than a semi-circular shape, including semi-oval, rectangular, or other regular or irregular shapes. Also, retraction portion 36 need not be linear between distal end 32 and proximal end 34, and can include one or more portions offset from one another between and distal end 32 and proximal end 34. Distal end 32 can be beveled to facilitate insertion through skin and tissue of the patient, although non-beveled configurations are also contemplated.

With references to FIGS. 6-10, further details of housing assembly 50 will be discussed. Housing assembly 50 includes a housing body 52 defining a first passage 54 for receiving elongate member 12 and a second opening or passage 56 for receiving connection portion 42 of arm 38. Housing assembly 50 includes a lever mechanism 80 that is releasably engageable to support member 12 to secure retractor member 30 in a desired translation position along support member 12. Housing assembly 50 further includes a translation member 90 that engages support member 12 and is operable to linearly translate retractor member 30 and housing assembly 50 along support member 12. Housing assembly 50 also includes a locking mechanism 150 that releasably engages mounting feature 44 of arm 38 to secure retractor member 30 to housing assembly 50. In addition, housing assembly 50 houses a drive mechanism 100 that is operable to pivot retractor member 30 relative to support member 12. Drive mechanism 100 includes a drive member 102 operably engaged to a rotary member 104 that is coupled to arm 38 of retractor member 30. When connection portion 42 of retractor member 30 is inserted into second passage 56 (FIG. 11), retractor member 30 and rotary member 104 pivot about center axis 45 (FIG. 4) of arm 38 via rotation of drive member 102. The arced channel 114 (FIG. 8) in rotary member 104 prevents rotary member 104 from contacting and being interfered by control member 140 during pivoting of retractor member 30. In another embodiment, control member 140 guide the movement of rotary member 104 and control member 140 provides a point of contact to assist in rotary member 104 pushing on connection portion 42 to rotate pivot retractor member 30 about center axis 45. This embodiment can be useful, for example, in embodiments of rotary member 104 with a bore 108 that does not match the geometry of connection portion 42 or otherwise does not encircle or capture arm 38 of retractor member 30.

Figure 10:
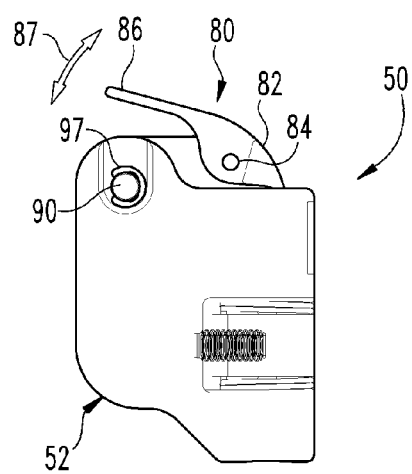
FIG. 10 is a plan view of the distal side of the housing assembly of FIG. 6.
Figure 16:
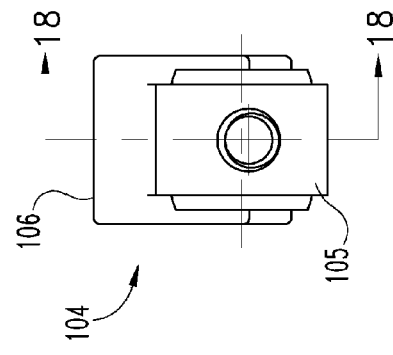
FIG. 16 is a left side elevation view of the rotation body of FIG. 15.
Figure 22:
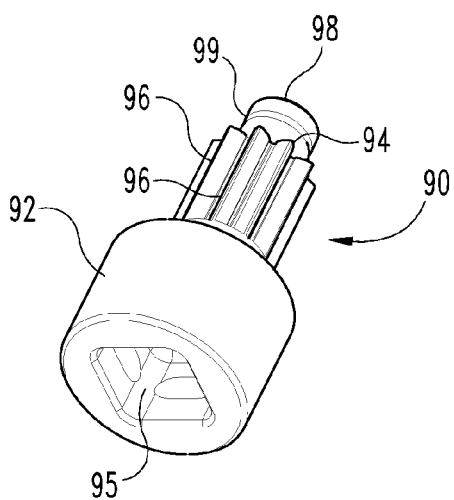
FIG. 22 is a perspective view of a translation member of the housing assembly of FIG. 6.
Figure 23:
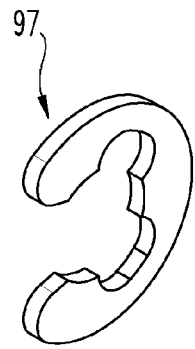
FIG. 23 is a perspective view of a retaining member of the housing assembly of FIG. 6.

Referring now further to FIGS. 11-14, housing 52 is shown in isolation from the other components of housing assembly 50. Housing 52 includes a body 58 defining first passage 54 adjacent to an outer side thereof that extends through and opens at opposite ends 58a, 58b of body 58. Body 58 includes a first receptacle 60 extending through proximal and distal sides 58c, 58d of body 58 to house translation member 90. Receptacle 60 opens into and is in communication with first passage 54 so that translation member 90 contacts the teeth or other features or surface on the outer side 20 of support member 12. As shown in FIG. 22, translation member 90 includes a head 92 and a shaft 94 extending from head 92 with longitudinal teeth 96 that interdigitate with teeth formed along the outer side 20 of support member 12 to translate housing assembly 50 and thus retractor member 30 along support member 12. Head 92 includes a recess 95 extending therein to receive a key or other driving tool to facilitate application of a driving force to translation member 90. The distal end 98 of translation member 90 includes a groove 99 extending therearound that receives a retaining ring 97, as shown in isolation in FIG. 23, to axially secure translation member 90 to housing body 52, as shown in FIG. 10, while allowing translation member 90 to rotate about its own longitudinal axis.

Housing body 52 also includes an outer flange 62 extending from the portion of body 52 that extends around first receptacle 60. As shown in FIGS. 6-7 and 9-10, lever mechanism 80 is mounted to flange 62. Lever mechanism 80 includes a lever member 82 pivotally mounted to flange 62 with a pivot pin 84. Lever member 82 includes a tab portion 86 at an outer end thereof and a contact portion 88 opposite tab portion 86. Lever member 82 is pivotal around pin 84 so that contact portion 88 extends from its locking position through a hole 55 of housing body 52 and into first passage 54 where it contacts the teeth or other structure along the outer facing side 20 of support member 12 to secure housing assembly 50 in a translated position along support member 12. Lever member 82 can be pivoted to a release position where tab portion 86 is depressed to pivot lever member 82 around pivot pin 84, as indicated by arrow 87, to disengage contact portion 88 and release housing assembly 50 from support member 12. A spring 89 extends into a well 64 of housing body 52 and contacts tab portion 86 to normally bias lever member 92 in locking engagement with support member 12. Spring 89 is compressed when tab portion 86 is pressed to release lever member 82 from support member 12.

Referring back to FIGS. 11-14, second passage 56 of housing body 52 opens at an inner lateral side 66 of housing body 52 facing retractor member 30 to receive connection portion 42 of arm 38. Housing body 52 also include a compartment 68 that opens at proximal side 58c of housing body 52 and houses drive mechanism 100 and locking mechanism 150 therein. Proximal side 58c can include a scale or other markings 72 thereon to indicate the amount of angulation of retractor member 30 relative to elongate member 12. Housing body 52 also includes a bore 74 for receiving a control member 140, as discussed further below.

Figure 8:
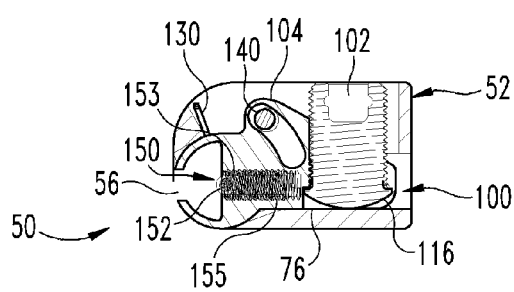
FIG. 8 is a section view of the housing assembly along line 8-8 of FIG. 6.
Figure 19:
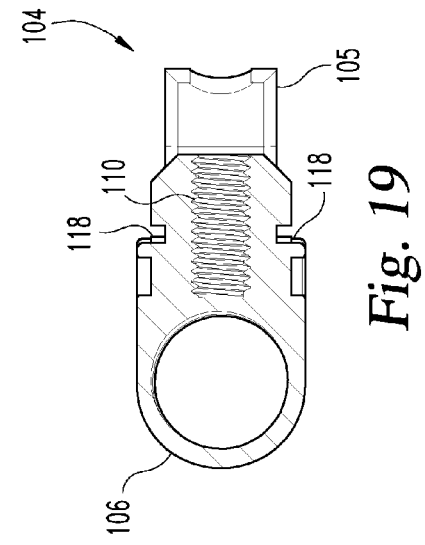
FIG. 19 is a section view of the rotation body along line 19-19 of FIG. 16.
Figure 17:
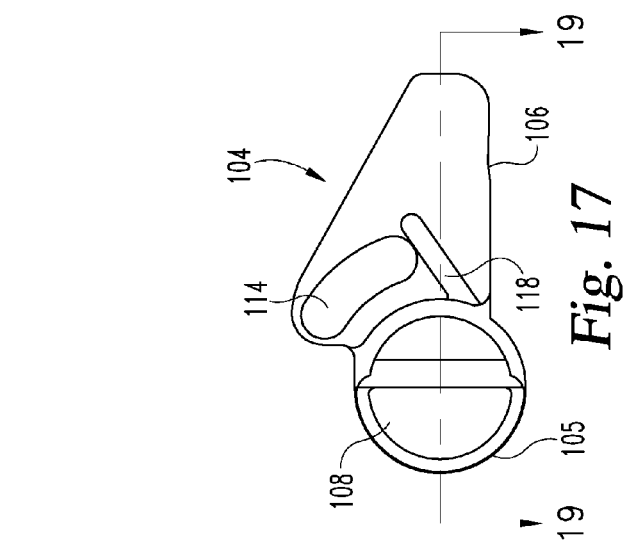
FIG. 17 is a plan view of the rotation body of FIG. 15.
Figure 15:
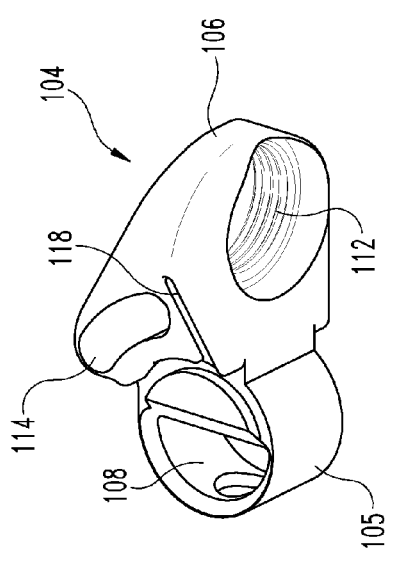
FIG. 15 is a perspective view of a rotation body of the housing assembly of FIG. 6.
Figure 18:
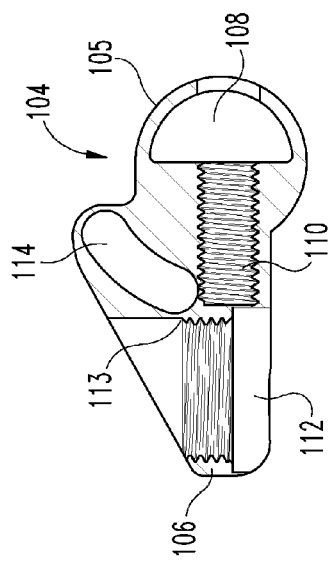
FIG. 18 is a section view of the rotation body along line 18-18 of FIG. 16.

FIGS. 15-19 show rotary member 104 of drive mechanism 100. Rotary member 104 includes a retractor arm receiving part 105 and a drive member mounting part 106. Receiving part 105 includes a ring-shape with a semi-circular bore 108 that receives the semi-circular connection portion 42 of arm 38 therein in a predetermined and fixed orientation. In another embodiment, arm 38 is integrally formed as one piece with rotary member 104. Mounting part 106 includes an internal threaded bore 110 extending from bore 108 that houses a ball plunger device of locking mechanism 150. In FIGS. 18-19, bore 110 extends in an oblique orientation to central axis 45. Alternatively, bore 110 can extend perpendicularly to central axis 45, such as shown in FIGS. 6-10 and FIGS. 24-25. In either arrangement, as shown in FIG. 8, the ball plunger device includes a ball member 152 that is biased to project into bore 108, but moves against the bias of spring 153 into bore 110 to allow insertion of connection portion 42 of arm 38 until mounting feature 44 is aligned with ball member 152. Locking mechanism 150 includes spring 153 to bias ball member 152 into mounting feature 44 to releasably lock retractor member 30 to housing assembly 50. A retaining shaft 155 is threadingly engaged in bore 110 to retain spring 153 and ball member 152 in internal bore 110. Other embodiments contemplate other forms for locking mechanism 150, including c-clips, locking pins, balseal springs, and morse tapers, for example.

Figure 20:
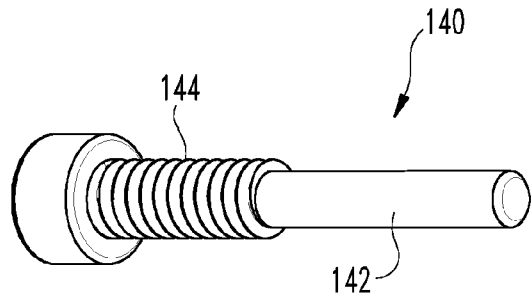
FIG. 20 is a perspective view of a control member of the housing assembly of FIG. 6.
Figure 21:
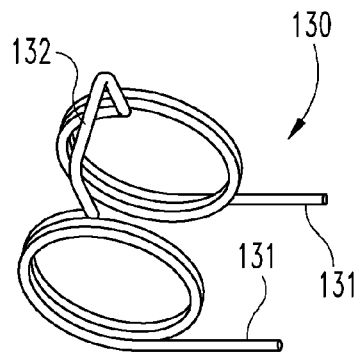
FIG. 21 is a perspective view of a biasing member of the housing assembly of FIG. 6.

Mounting part 106 also includes a drive member receptacle 112 with an internal thread profile 113. Drive member receptacle 112 is orthogonally oriented to bore 108 and faces the proximal side opening of compartment 68 so that drive member 102 is accessible by the user when drive member 102 is engaged in receptacle 112. Mounting part 106 also includes an arced channel 114 extending through opposite sides of rotary member 104. Arced channel 114 receives a non-threaded part 142 of control member 140, which is shown in isolation in FIG. 20. Threaded part 144 of control member 140 is threadingly engaged to bore 74 of housing body 52 and extends therefrom so that non-threaded part 142 is located through arced channel 114 of rotary member 104. Drive member 102 is threadingly engaged in receptacle 112 and is rotated therein to displace rotary member 104 around center axis 45 of arm 38 of retractor member 30. As shown in FIG. 8, drive member 102 includes a cam head 116 that contacts and pivots along an inner surface 76 of housing body 52 adjacent distal side 58d as rotary member 104 moves around control member 140 and center axis 45. Mounting part 106 of rotary member 104 also includes grooves 118 on opposite sides thereof that receive a portion of a biasing member 130, shown in FIG. 21. In FIG. 21, biasing member 130 is a torsion spring with legs 131 positioned in grooves 118. A bridge member 132 of biasing member 130 connects legs 131. Biasing member 130 extends between and contacts rotary member 104 with legs 131 and contacts housing body 52 with bridge member 132 to normally bias rotary member 104 and thus retractor member 30 toward a neutral position in its first or initial orientation.

As indicated above, first and second retractor members 30, 1030 can be moved along elongate support member 12 to adjust the spacing between first and second retractor members 30, 1030. In view of the foregoing description, it should be appreciated that retractor assembly 10 is configured such that first and second retractor members 30, 1030 can be pivoted or rotated away from one another about their proximal ends 34, 1034 to provide working channel 24 with a tapered configuration that reduces in size from the distal ends 32, 1032 of retractor members 30, 1030 through the skin to the proximal ends 34, 1034 of retractor members 30, 1030.

Figure 24:
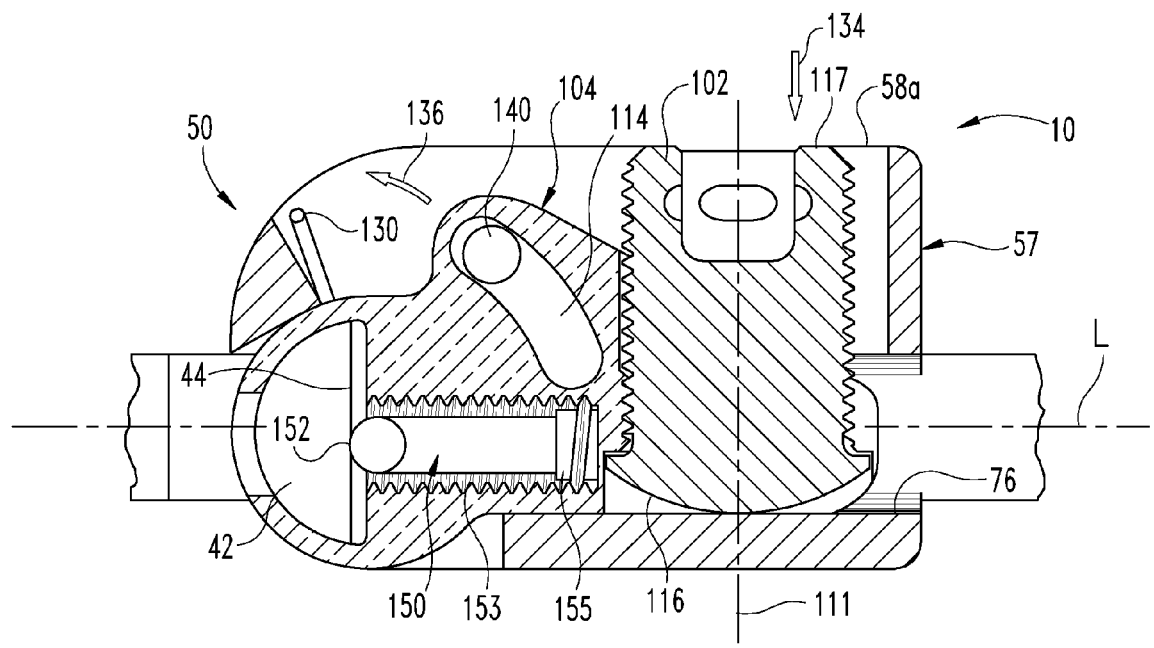
FIG. 24 is a section view of the housing assembly through the drive member with the retractor member of the retractor assembly engaged to the housing assembly in a neutral orientation.
Figure 25:
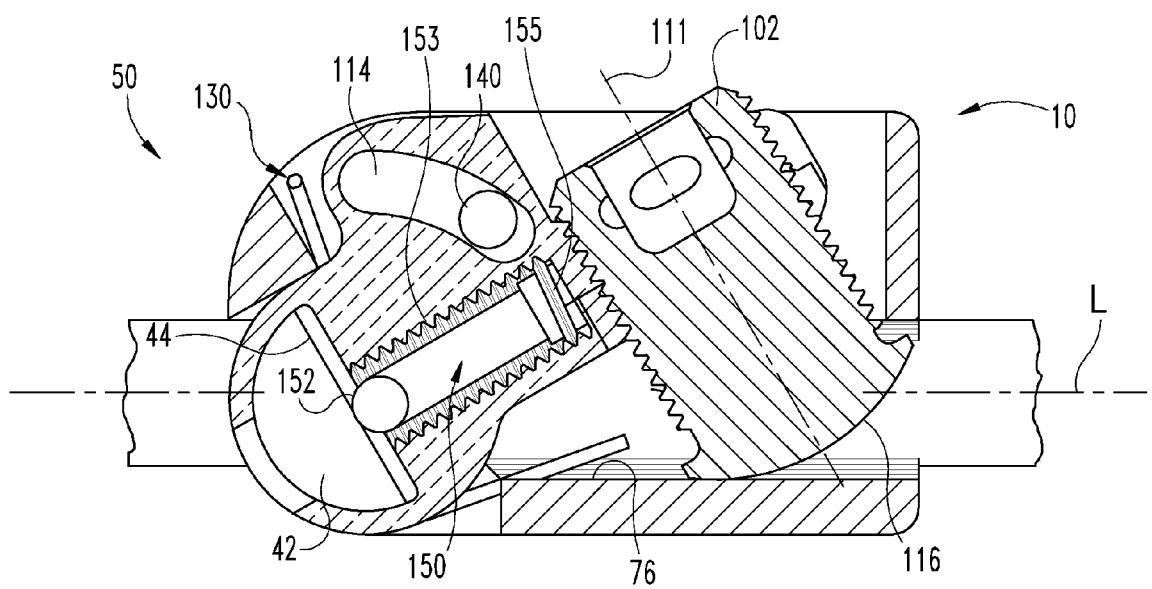
FIG. 25 is a section view of the housing assembly through the drive member with the retractor member of the retractor assembly engaged to the housing assembly in a pivoted orientation.

More particularly, when drive member 102 is rotated it translates on its central axis 111 in a direction indicated by arrow 134 along rotary body 104 and cam head 116 contacts housing body 52, which in turn rotates rotary body 104 along control member 140 is a direction indicated by arrow 136 and as shown from FIG. 24 to FIG. 25. Control member 140 extending through arced channel 114 maintains rotary member 104 within housing 52 when arm 38 of retractor member 30 is not inserted in second passage 56. Translation of drive member 102 and rotation of rotary member 104 causes a separation distance between distal ends 32, 1032 of retractor members 30, 1030 to increase, as shown from FIG. 1 to FIG. 2. Cam head 116 of drive member 102 also pivots along inner surface 76 so that drive member 110 follows rotation of rotary member 104, causing drive member 102 to pivot as rotary member 104 rotates so that central axis 111 moves from a first orientation, such as shown by the perpendicular orientation in FIG. 24, with longitudinal axis L to a second orientation as shown in FIG. 25. In the illustrated embodiment, the change in angular orientation follows the change in angular orientation of retractor member 30 to longitudinal axis L. Moreover, the threaded engagement between drive member 102 and rotary member 104 allows a user to incrementally increase the separation distance between distal ends 32, 1032 of retractor members 30, 1030 and provides infinitely small adjustment capabilities. This allows the surgeon to avoid over-retraction of muscle tissue, in contrast to systems that only provide fixed increments of angular adjustment for the retractor member.

Drive member 102 includes a proximal end 103 opposite cam head 116 that, in at least the initial position of retractor member 30, is recessed distally of proximal side 58a. Translation and pivoting of retractor member 30 using translation member 90 and drive member 102 can be accomplished with a removable key or other suitable driving device that can be readily engaged to and disengaged from translation member 90 and drive member 102. This provides a housing assembly 50 that is free of protrusions or other obstructions extending proximally from proximal side 58a which have the potential to interfere with the surgeon during surgery. In addition, second passage 56 of housing body 52 and bore 108 of rotary member 104 allow connection portion 42 of arm 38 to be positioned in an endwise manner in a fixed, predetermined orientation into housing assembly 50 to engage with locking mechanism 150. Insertion of arm 38 is aided since the surgeon can visualize from inner side 66 of housing body 52 the insertion location of arm 38 into housing 52.

Additionally, among other things, a tapered working channel 24 provides the surgeon greater access and increased visualization of the surgical site while minimizing tissue retraction at the skin level. The tapered working channel 24 also allows greater angulation of instruments and implants placed through working channel 24, more selection in positioning of instruments and implants within working channel 24, and the ability to position instruments and implants adjacent the inner wall surfaces of the separated first and second retractor members 30, 1030 to increase the room available at the surgical site for multiple instruments and for orienting implants. The biasing of rotary member 104 to its initial position with biasing member 130 facilitates the return of retractor members 30, 1030 to their initial, neutral position when the drive member 102 is rotated in the reverse direction. Alternatively, a lever type mechanism can be provided to pivot retractor member 30. A lever mechanism provides the surgeon tactile feedback during tissue retraction. Once the retractor member 30 is pivoted with the lever mechanism, drive member 102 is translated to contact inner side of housing 76 to maintain the pivoted orientation of retractor member 30 achieved with the lever mechanism.

In addition, in the illustrated embodiment, retraction portion 36 has a neutral, initial position that is perpendicular or substantially perpendicular to elongate member 12 and its longitudinal axis L. In other embodiments, the retraction portion can be angled relative to support member 12 and longitudinal axis L in the neutral position. For example, retraction portions 36, 1036 can be configured to have a "toe-in" orientation in the neutral insertion position so that distal ends 32, 1032 are closer to one another than proximal ends 34, 1034. One or more of retraction portions can then be pivoted from the "toe-in" orientation to a "toe-out" orientation so increase the size of working channel 24 at distal ends 32, 1032. In still other embodiments, the orientation of drive mechanism 100 can allow the retractor members 30, 1030 to move from an initial orientation toward a "toe-in" configuration. In yet another embodiment, the retractor member 30, 1030 have a neutral position that is non-perpendicular to longitudinal axis L but with retractor members 30, 1030 normally parallel to one another. For example, one retractor member 30, 1030 can be arranged to "toe-in" and the other arranged to "toe-out" by approximately the same angle. Adapters (not shown) could be provided to allow the blades to be engaged to housing assembly 50 in various starting/neutral positions.

In use of retractor assembly 10, retractor members 30, 1030 are insertable through an incision in skin and tissue of a patient to provide working channel 24 to a surgical site. It is contemplated that retractor members 30, 1030 are inserted through skin and tissue in an insertion configuration for working channel 24. In the insertion configuration, working channel 24 is substantially enclosed or circumscribed by retractor members 30, 1030. After insertion into the patient, working channel 24 can be enlarged by separating first retractor member 30 and second retractor member 1030. Separation of retractor members 30, 1030 increases the size of working channel 24 from distal ends 32, 1032 to proximal ends 34, 1034.

Working channel 24 can have a size in the insertion configuration that allows passage of one or more surgical instruments and/or implants to the surgical location in the patient's body. It may be desirable during surgery to provide greater access to the surgical site in the patient's body beyond the locations provided through working channel 24 in its insertion configuration. At least one of first retractor member 30 and second retractor member 1030 are movable away from the other to enlarge working channel 24. In the enlarged configuration of working channel 24, a space is formed between the adjacent longitudinal edges of retractor members 30, 1030. The space between the adjacent longitudinal edges exposes enlarged working channel 24 to skin and tissue of the patient between the separated first retractor member 30 and second retractor member 1030. This exposed tissue can also be accessed by the surgeon through the enlarged working channel 24 with one or more instruments and/or implants. It is further contemplated that a shield, guard or tissue retractor could be placed in enlarged working channel 24 to maintain the exposed tissue away from the enlarged working channel 24. Various non-limiting examples of additional tissue retractors that can be positioned in the enlarged working channel 24 between retractor members 30, 1030 are provided in U.S. Pat. Nos. 7,473,222 and 7,513,869 to Branch et al., the contents of which are incorporated herein by reference in their entirety.

Viewing instruments can be positioned in or adjacent to working channel 24 to facilitate surgeon viewing of the surgical site. For example, an endoscopic viewing element can be mounted on the first end of one of retractor members 30, 1030 with a scope portion extending along working channel 24. A microscopic viewing element can be positioned over the first end of one of retractor members 30, 1030 for viewing the surgical site. Other imaging techniques, such as lateral fluoroscopy, can be used alone or in combination with the endoscopic and microscopic viewing elements. Retractor members 30, 1030 can receive a light source to allow viewing with naked eye visualization and/or loupes. It is further contemplated that other instruments can be mounted on the first end of one or both of retractor members 30, 1030, such as nerve root retractors, tissue retractors, forceps, cutter, drills, scrapers, reamers, separators, rongeurs, taps, cauterization instruments, irrigation and/or aspiration instruments, illumination instruments, inserter instruments, and the like for use in surgical procedures at the surgical site. Such viewing instruments and other instruments can be employed with working channel 24 in its initial insertion configuration and/or its enlarged configuration.

In one non-illustrated form, retractor members 30, 1030 may be structured to align and releasably couple with one another in the insertion configuration. For example, retractor member 30 can include an alignment pin structured to engage with a corresponding alignment aperture on retractor member 1030. Similarly, retractor member 1030 may include an alignment pin structured to engage with a corresponding alignment aperture on retractor member 30. Other arrangements are also contemplated for aligning and releasably coupling first retractor member 30 and second retractor member 1030 to one another. Examples of such arrangements include dovetail connections, fasteners, threaded coupling members, clamping members, snap rings, compression bands, straps, ball-detent mechanisms, and releasably interlocking cams or tabs, just to name a few possibilities.

First retractor member 30 has a perimeter length for retraction portion 36 across proximal end 34 which can be about the same as the perimeter length of retraction portion 36 across distal end 32. Retraction portion 1036 of second retractor member 1030 includes a perimeter length across proximal end 1034 which can be about the same as the perimeter length of retraction portion 1036 across distal end 1032. Retraction portions 36, 1036 can have a semi-circular cross-section, and form a generally circular cross-section for the working channel 24 when placed adjacent one another in the insertion configuration. Other cross-sectional shapes are also contemplated for first and second retraction portions 36, 1036, such as, for example, any open sided polygonal shape, curved shape, or combined curved/polygonal shape. When retraction portions 36, 1036 are separated from one another, working channel 24 can have a cylindrical or frusto-conical shape with, for example, a cross-section that is oval, elliptical, circular, curved, polygonal, or combined polygonal/curved in shape.

Retractor members 30, 1030 can be provided with sufficient rigidity between their distal and proximal ends to separate and maintain separation of tissue when retractor members 30, 1030 are initially inserted and also when the tissue is retracted by moving at least one of first retractor member 30 and second retractor member 1030 away from the other. For example, retraction portions 36, 1036 can include a thickness which provides sufficient rigidity to resist bending or bowing under the forces exerted on it by the retracted tissue. Also, the semi-circular shaped cross-section of retraction portions 36, 1036 can be configured to provide a sufficient section modulus or moment of inertia in the direction of movement of retractor members 30, 1030 to resist bending, bowing and/or deflection forces applied during such movement.

One particular application for retractor assembly 10 is in spinal surgery. It is contemplated that, after insertion of retractor members 30, 1030, they are separated predominantly in one direction to retract muscle and tissue which extends between first and second retractor members 30, 1030. For example, first and second retractor members 30, 1030 can be primarily or predominantly separable by translation and/or pivoting in the direction of the spinal column axis. The muscle tissue adjacent the spine has a fiber orientation that extends generally in the direction of the spinal column axis. The separation of retractor members 30, 1030 can also separate the muscle tissue along the fibers, thus the amount of separation and the resultant tearing and trauma to the muscle tissue can be minimized. It is also contemplated in other techniques employing retractor assembly 10 that working channel 24 can be enlarged primarily in a direction other than along the spinal column axis or in areas other than spine.

In one example, a method for positioning retractor members 30, 1030 through the skin and tissue includes making an incision through skin adjacent the location of a surgical site. For example, in spinal surgery, the incision can be made at a vertebral level at a location that provides access to the disc space between adjacent vertebrae or to one or more vertebra through a desired approach. Prior to insertion of retractor members 30, 1030, the skin and tissue can be sequentially dilated via a dilation instrument set (not illustrated) which can include guidewires and/or one or more tissue dilators of increasing size. The tissue dilators are inserted one over another to form a pathway through the skin and tissue to the surgical site in the patient. In such procedures, retractor members 30, 1030 are positioned over or through the last inserted dilator to form the pathway in the skin and tissue. Working channel 24 through retractor members 30, 1030 provides access to the surgical site at the distal ends 32, 1032 of retractor members 30, 1030 when the guidewires and dilators, if used, are removed therefrom. In yet other embodiments, retractor members 30, 1030 can be inserted using a speculum or speculum-type device to create the initial pathway. For example, retractor members 30, 1030 with flat retraction portions can be inserted with such devices.

For the entire surgery or for certain procedures during the surgery, it may be desired by the surgeon to increase the size of working channel 24 to facilitate access to the surgical site. First and second retractor members 30, 1030 of retractor assembly 10 can be separated from their insertion configuration to a separated configuration in which working channel 24 is enlarged. Even in the separated configuration, at least one of first retractor member 30 and second retractor member 1030 can be moved by translation and/or pivoting away from the other to change or adjust the size and/or shape of working channel 24. Adjacent ones of the edges of retraction portions 36, 1036 are separated and working channel 24 is exposed to skin and tissue while first and second retractor members 30, 1030 hold tissue out of the operative field.

Figure 26:
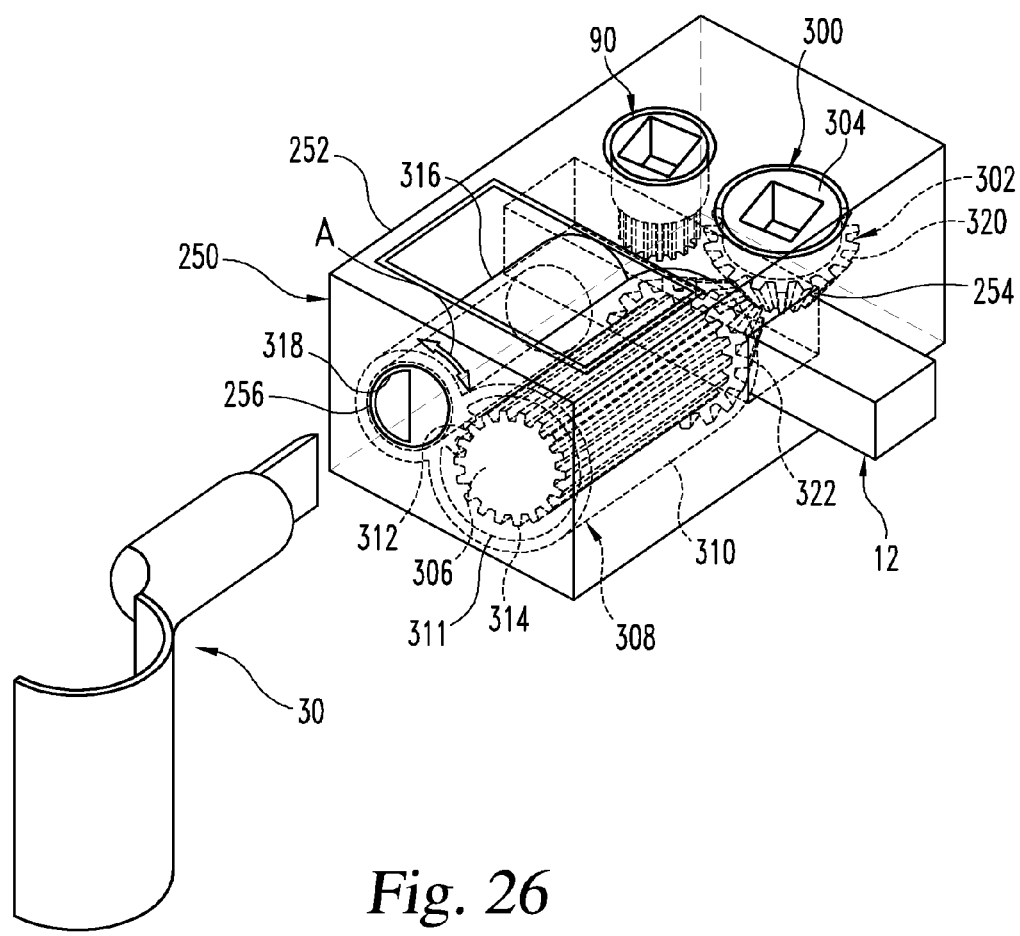
FIG. 26 is an exploded perspective view of a portion of another embodiment retractor assembly.

FIGS. 26-31 illustrate various other configurations for retractor assemblies that are operable to pivot and/or translation a retractor member relative to a support member and that include a housing assembly that houses a low profile drive mechanism that is unobstructive to the surgeon during surgery. Unless specifically noted, it is contemplated that these embodiment retractor assemblies can include any one or combination of the features of retractor assembly 10 discussed above. In FIG. 26, retractor member 30 is shown in exploded form from another embodiment housing assembly 250 and drive mechanism 300. It should be understood that a minor image of the housing assembly 250 and drive mechanism could be provided for retractor 1030, although identical housing assemblies and drive mechanisms are not required. Housing assembly 250 includes a housing body 252 defining a first passage 254 opening at opposite ends thereof for receiving support member 12 and a second passage 256 opening at an inner lateral side thereof for receiving connection portion 42 of retractor member 30. Housing body 252 may house an optional translation mechanism 90 that is flush or recessed in and accessible from the proximal side of housing body 252 to translate housing assembly 250 and retractor member 30 along support member 12.

Drive mechanism 300 includes a drive member 302 housed and rotatable in housing body 252 and a rotary member 308 that is housed in and rotatable in housing body 252 that is engaged to drive member 302. Drive member 302 includes a pinion 304 that is flush or recessed relative to the proximal side of housing body 252. Drive member 302 also includes a shaft 306 rotatable mounted to housing body 252 about an axle so that shaft 306 extends transversely to pinion 304 and is operably engaged to pinion 304. Rotary member 308 includes a mounting part 310 that defines a bore or receptacle 311 for receiving shaft 306 and also includes teeth or splines 312 projecting into receptacle 311 that interdigitate with teeth or splines 314 along shaft 306. Receptacle 311 can be enlarged relative to shaft 306 to provide room for rotary member 308 to travel as shaft 306 is rotated to displace rotated member 308 via the engagement between teeth 312, 314. Rotary member 308 also includes a receiving part 316 that defines a bore 318 that is complementary in shape to the shape of connection portion 42 of arm 38 of retractor member 30. In operation, beveled gear 320 at the distal end of pinion 304 engages beveled gear 322 at the adjacent end of shaft 306 so that as pinion 304 is rotated about its central axis, shaft 306 also rotates about its central axis to rotate rotary member 308 and thus pivot retractor member 30 along an arced path A. Receptacle 311 of rotary member 308 can be enlarged and parallel arced path A to accommodate displacement of rotary member 308 along shaft 306 as rotary member 308 rotates.

Figure 27A:
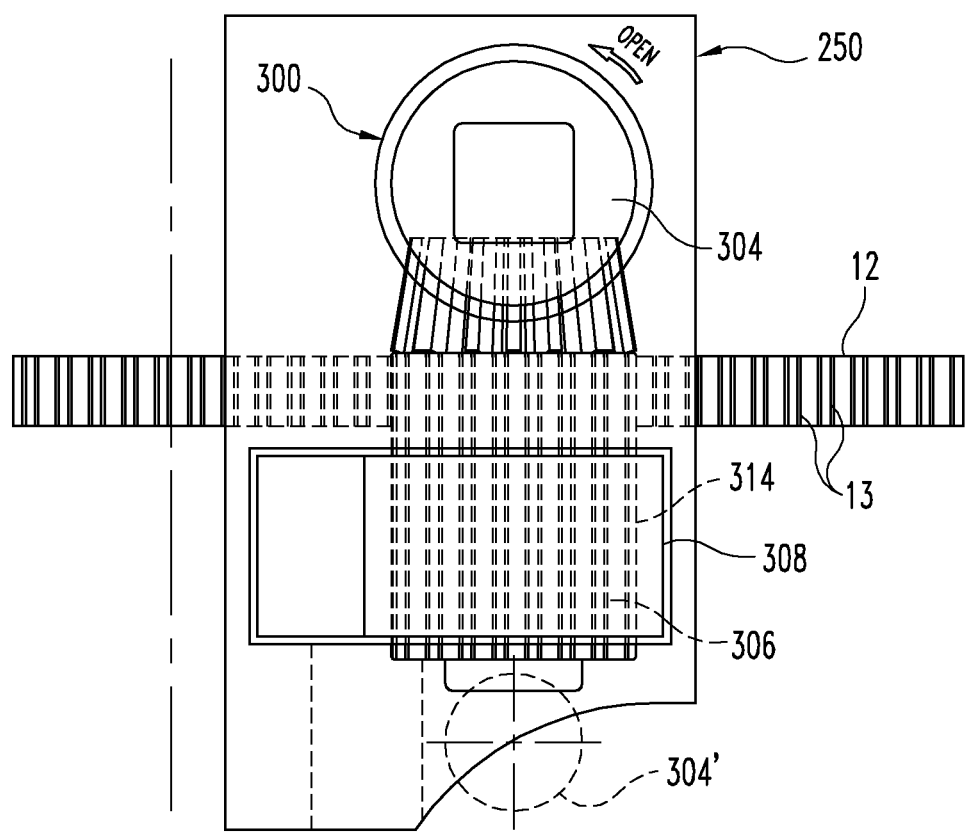
FIG. 27A is a plan view of a portion of a support member and housing assembly of another embodiment retractor assembly.
Figure 27B:
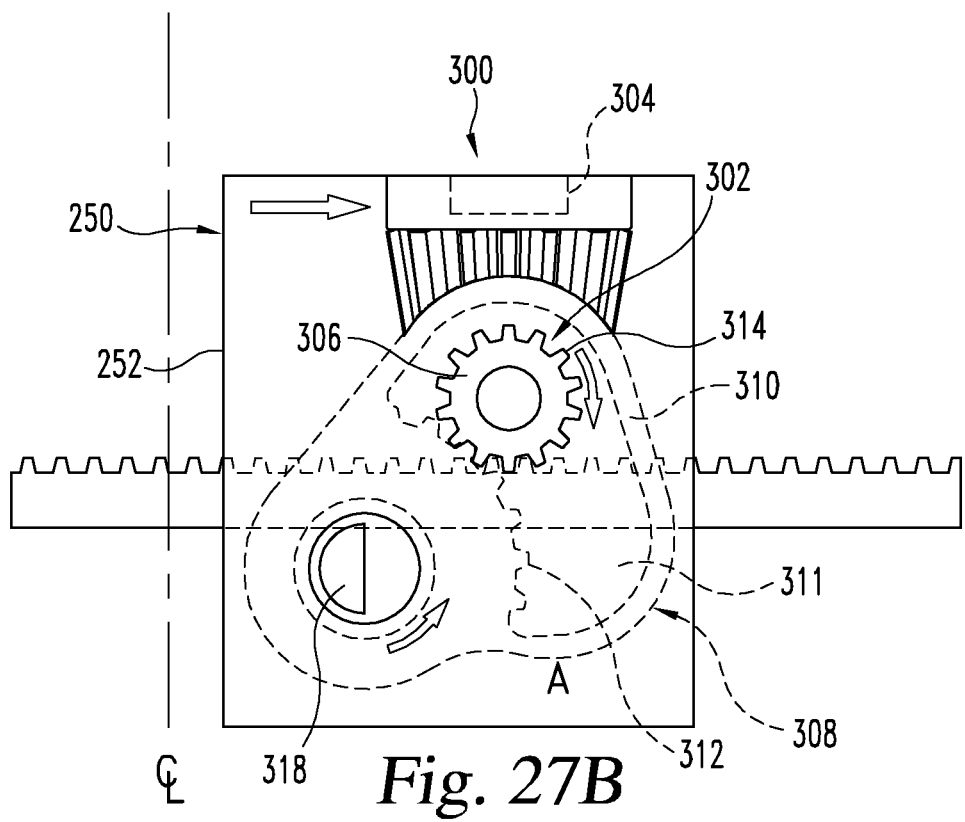
FIG. 27B is an elevation view of the portion of the support member and housing assembly of the retractor assembly in FIG. 27A.

FIGS. 27A and 27B show an alternate configuration for the FIG. 26 embodiment with a shaft 306' that is elongated and positioned relative to housing body 252 so that splines 314 of shaft 306' also engage teeth 13 along an elongated embodiment of support member 12. Thus, the embodiment of FIGS. 27A and 27B provides for simultaneous translation and pivoting of retractor member 30 along and relative to support member 12. In yet another variation of this embodiment, pinion 304 could be located adjacent the opposite end of shaft 306 and engaged to a beveled gear arrangement provided there, as indicated diagrammatically by pinion 304'.

Figure 28A:
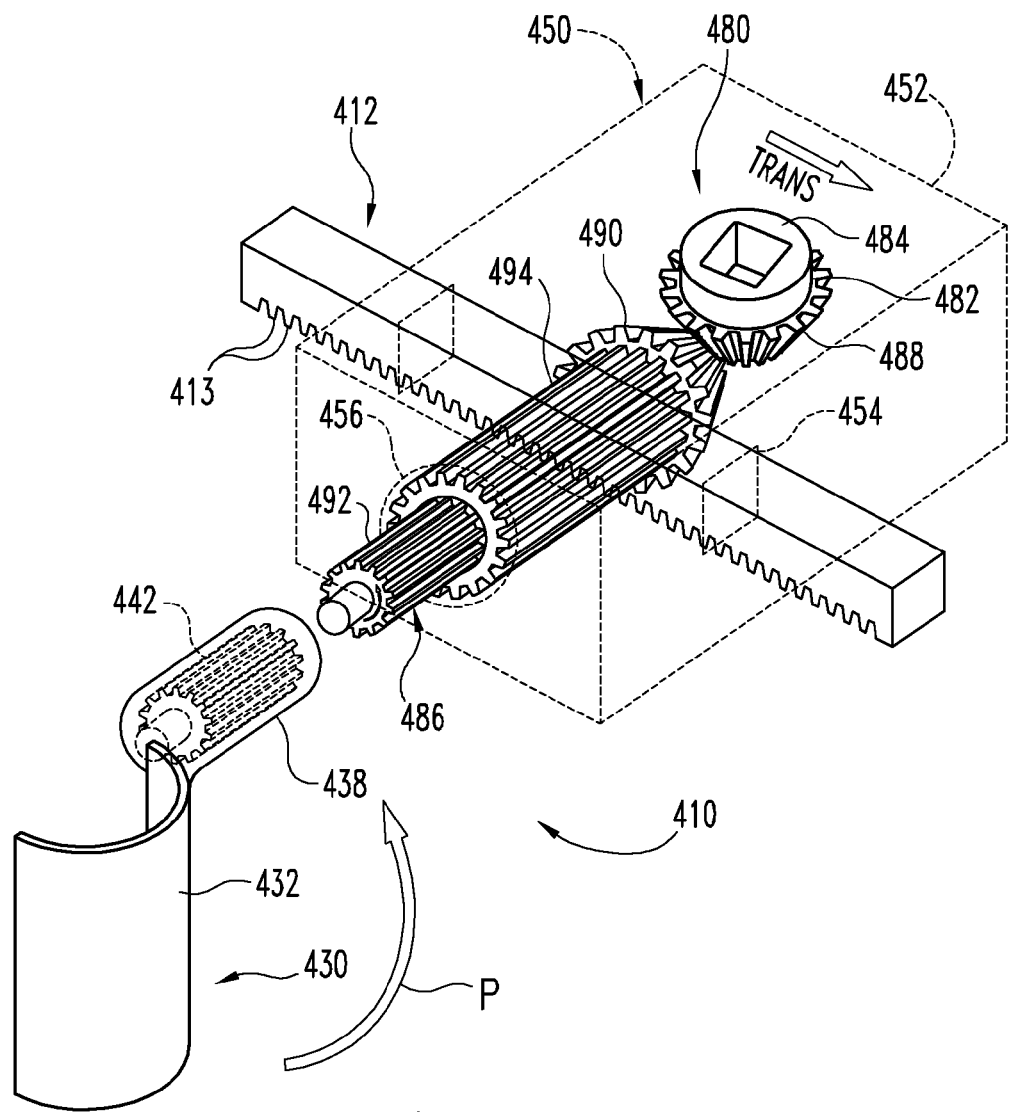
FIG. 28A is an exploded perspective view of a portion of another embodiment retractor assembly.
Figure 28B:
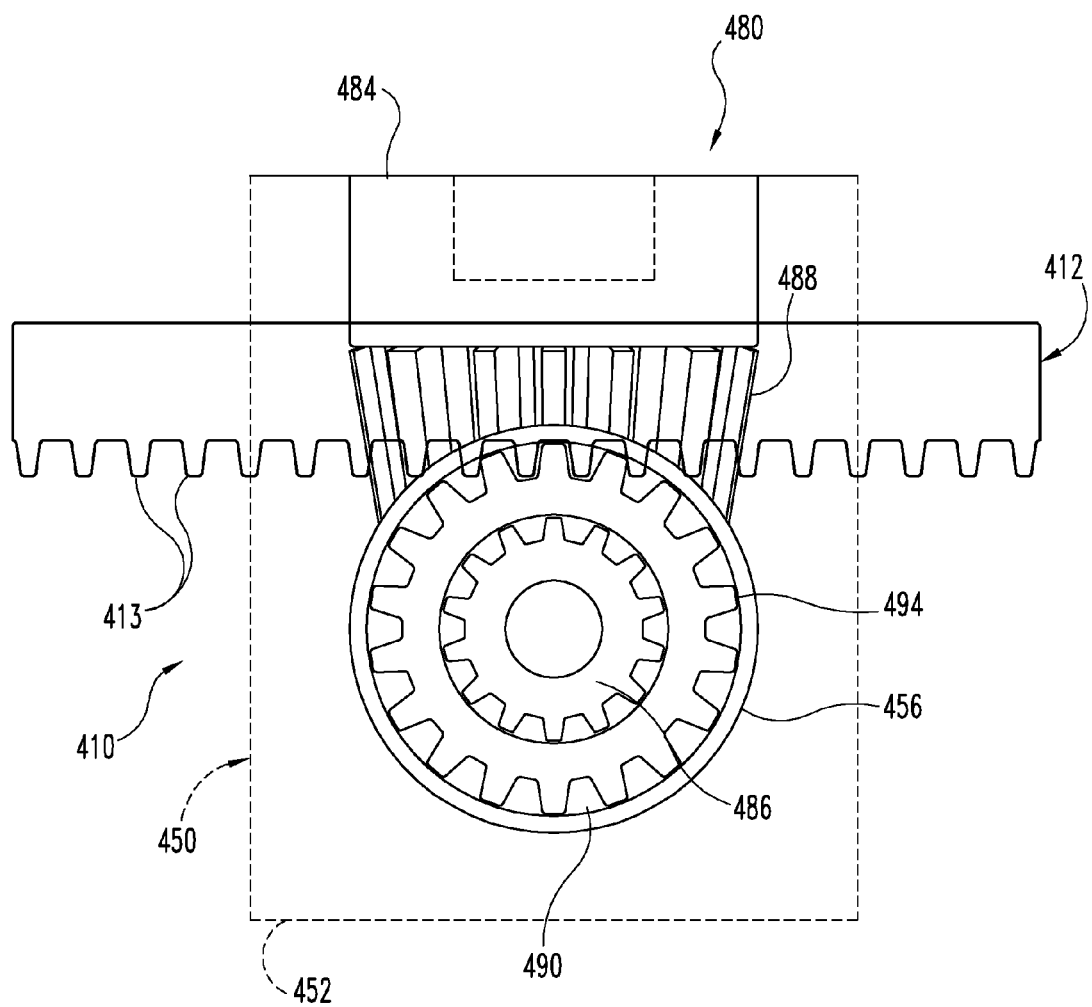
FIG. 28B is an elevation view of the housing assembly and support member of the retractor assembly of FIG. 28A.

FIGS. 28A and 28B show an exploded perspective view and partial elevation view, respectively, of a portion of another embodiment retractor assembly. In this embodiment, retractor assembly 410 includes an elongated support member 412 with teeth 413 along a distal side thereof. Retractor assembly 410 also includes a retractor member 430 with a retractor portion 432 and an arm 438 extending transversely from a proximal end of retractor portion 432. Arm 438 includes a connection portion 442 with an internal bore defining a female spline geometry to mate with drive mechanism 480 carried by housing assembly 450.

Retractor assembly 410 includes housing assembly 450 defining a housing body 452 with a first passage 454 opening at opposite ends thereof for receiving support member 412 and a second passage 456 opening at the inner lateral side thereof for an extension of drive mechanism 480. Drive mechanism 480 includes a drive member 482 having a pinion 484 accessible through the proximal side of housing body 452 and a shaft 486 extending transversely to pinion 484 through the opening of second passage 456 at the inner lateral side of housing body 452. Pinion 484 is flush or recessed relative to the proximal side of housing body 452 to eliminate protrusions from housing body 452. Pinion 484 includes a bevel gear end 488 that is operably engaged to a beveled gear end 490 of shaft 486. The opposite end 492 of shaft 486 includes a male spline configuration that slidingly receives connection portion 442 of arm 438 therearound. The interdigitating splines cause retractor member 430 to follow shaft 486 and pivot as indicated by arrow P as pinion 484 is rotated to drive shaft 486 around its central axis. Furthermore, shaft 486 includes splines 494 around an intermediate portion thereof that engage teeth 413 of support member 412. As shaft 486 rotates, housing assembly 450 and retractor member 430 translate along support member 412 simultaneously with the pivoting of retractor member 430. In this embodiment, drive mechanism 480 is directly engaged to retractor member 430 without a rotary member linking the drive member and retractor member.

Figure 29:
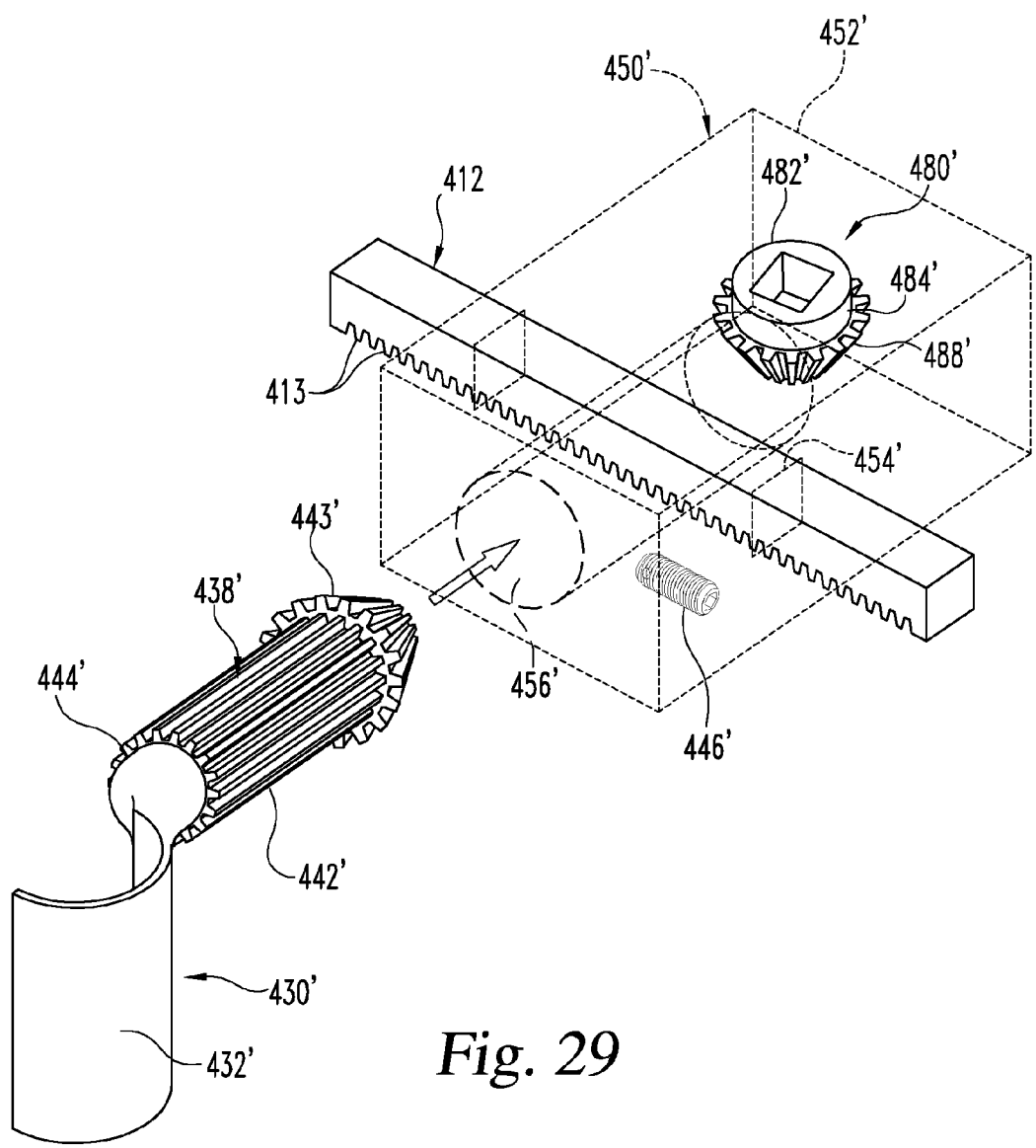
FIG. 29 is an exploded perspective view of a portion of another embodiment retractor assembly.

FIG. 29 shows an alternate configuration of the FIGS. 28A and 28B embodiment in which the shaft of the drive member is incorporated into arm 438' of retractor member 430'. Arm 438' includes a connection portion 442' with splines extending longitudinally therearound and a bevel gear end 443' at the outer end of arm 438'. Arm 438' also includes a retaining feature 444' adjacent its connection with retractor portion 432'. In the illustrated embodiment, retaining feature 444' is a circumferential groove that releasably receives a locking mechanism 446' of housing assembly 450' therein.

Housing assembly 450' includes a housing body 452' with a first passage 454' for receiving support member 412 therethrough and a second passage 456' for receiving arm 438' therein. Drive mechanism 480' includes a drive member 482' in the form of pinion 484' having a distal bevel gear end 488' operably engaged to bevel gear end 443' of arm 438'. As pinion 484' is rotated about its central axis, gear end 488' causes arm 438' to rotate about its central axis to pivot retractor member 430'. Furthermore, the splines around connection portion 442' engage teeth 413 of support member 412 to translate retractor member 430' along support member 412 simultaneously with the pivoting of retractor member 430'.

Figure 30A:
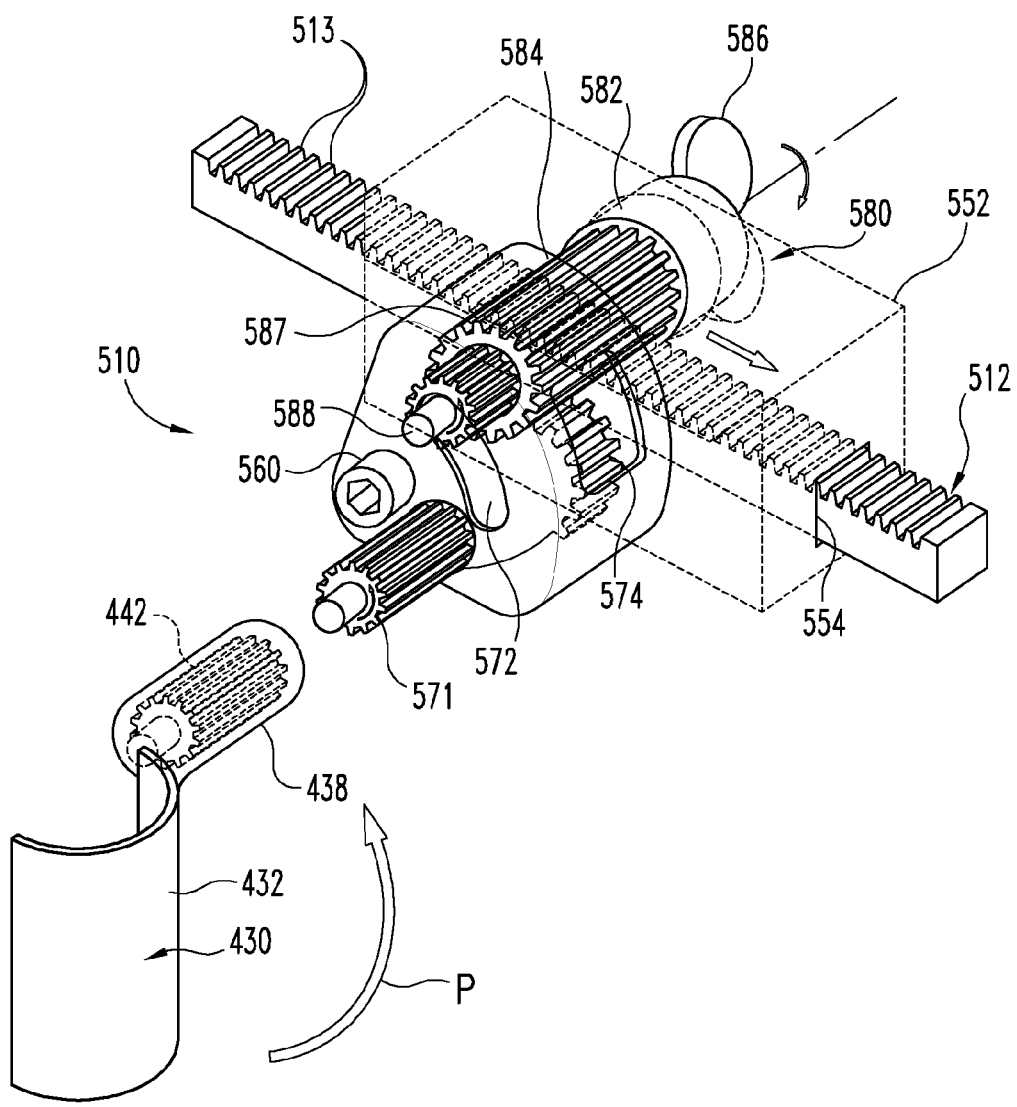
FIG. 30A is an exploded perspective view of a portion of another embodiment retractor assembly.
Figure 30B:
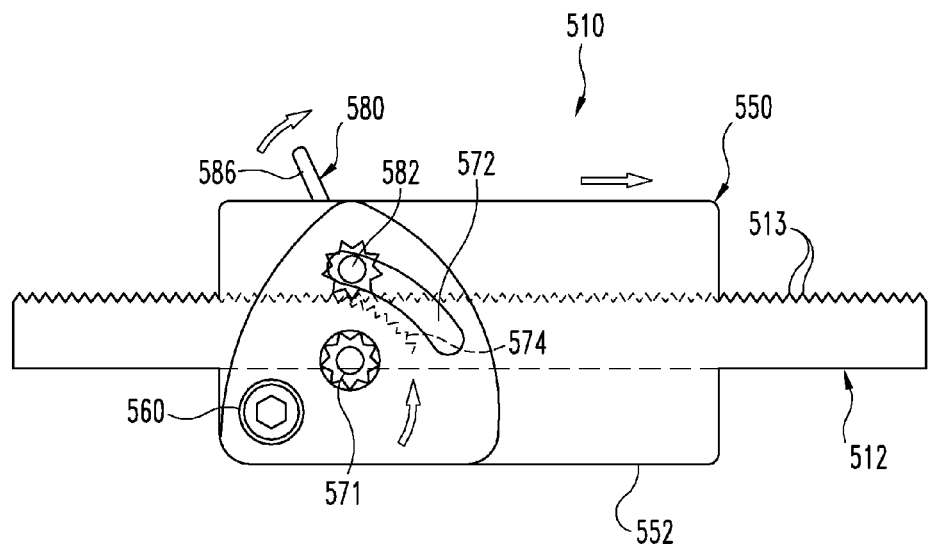
FIG. 30B is an elevation view of the housing assembly and support member of the retractor assembly of FIG. 30A.

Referring to FIGS. 30A and 30B, there is shown a portion of another embodiment retractor assembly 510 that utilizes retractor member 430 of FIG. 28A. Retractor assembly 510 includes a housing assembly 550 that supports a drive mechanism 580 and an external rotary member 570. Housing assembly 550 includes a housing body 552 with a first passage 554 that receives an elongate support member 512. Drive mechanism 580 includes a drive member 582 extending through a second passage of housing body 552 in a transverse relationship to support member 512. Drive member 582 includes a splined shaft 584 that interdigitates and engages teeth 513 along support member 512. A key 586 is removably engaged to drive member 582 on an outer lateral side of support member 512 and is accessible by the surgeon to rotate drive member 582 and translate housing assembly 550 and retractor member 430 along support member 512.

Rotary member 570 is rotatably mounted to housing body 552 with rotation fastener 560. Rotary member 570 includes an externally splined mounting shaft 571 to receive and interdigitate with connection feature 442 of retractor member 430 so that retractor member 430 does not rotate relative to rotary member 570. Fastener 560 allows rotary member 570 to rotate therearound. Rotary member 570 also includes an arced window 572 that receives a control portion 588 of drive member 582 therein. A plurality of teeth 574 are formed by rotary member 570 in window 572 that are engaged by splined shaft 584 with an intermediate portion 587 of splined shaft 584 extending through arced window 572 to maintain control of rotary member 570 as it rotates around rotation fastener 560 and pivots retractor member 430 as retractor member 430 is simultaneously translated along support member 512.

Figure 31:
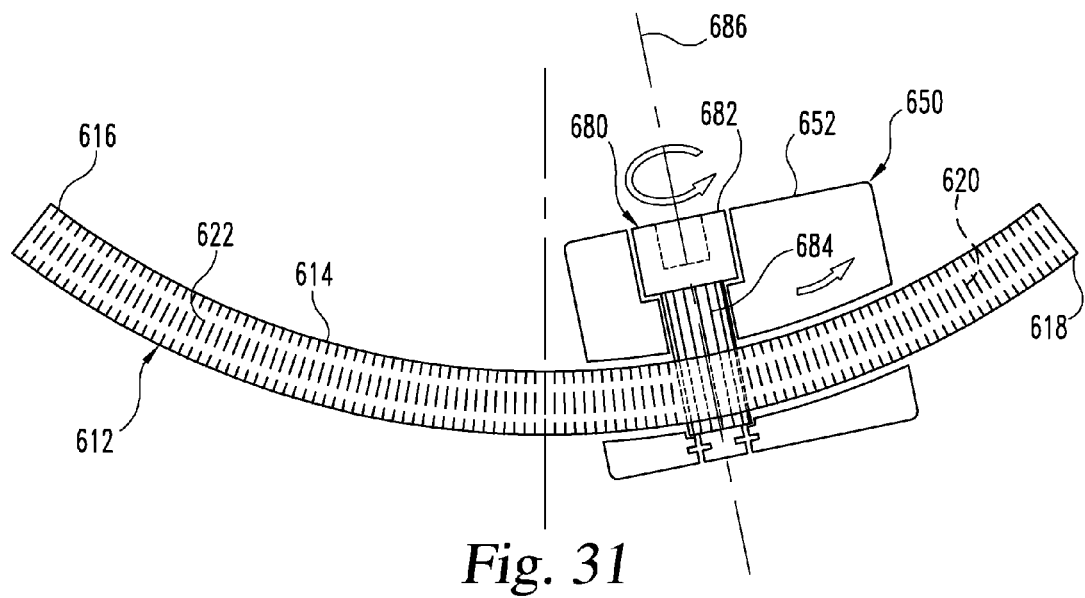
FIG. 31 is elevation view of a housing assembly and support member of another embodiment retractor assembly.

FIG. 31 shows another embodiment support member 612 and housing assembly 650 for simultaneously pivoting and translation of a retractor member. Support member 612 includes an elongated body 614 that is curved along its longitudinal axis to define an arc between ends 616, 618. In use, support member 612 is positioned so that its convex side faces distally toward the patient. Body 614 also includes teeth 620 along a lateral side 622 of support member 612 that engage drive mechanism 680 of housing assembly 650. Drive mechanism 680 includes a drive member 682 in the form of a pinion with splines 684 that interdigitate and engage teeth 620 to translate housing assembly 650 and the retractor member engaged thereto along support member 612 as drive member 682 is rotated about its central axis 686. Drive member 682 is recessed or flush to the proximal side 655 of housing body 652 to eliminate protrusions from housing assembly 650 that may interfere with the surgeon.

Any theory, mechanism of operation, proof, or finding stated herein is meant to further enhance understanding of the present application and is not intended to make the present application in any way dependent upon such theory, mechanism of operation, proof, or finding. It should be understood that while the use of the word preferable, preferably or preferred in the description above indicates that the feature so described may be more desirable, it nonetheless may not be necessary and embodiments lacking the same may be contemplated as within the scope of the application, that scope being defined by the claims that follow. In reading the claims it is intended that when words such as "a," "an," "at least one," "at least a portion" are used there is no intention to limit the claim to only one item unless specifically stated to the contrary in the claim. Further, when the language "at least a portion" and/or "a portion" is used the item may include a portion and/or the entire item unless specifically stated to the contrary.

While the application has been illustrated and described in detail in the drawings and foregoing description, the same is to be considered as illustrative and not restrictive in character, it being understood that only the selected embodiments have been shown and described and that all changes, modifications and equivalents that come within the spirit of the application as defined herein or by any of the following claims are desired to be protected.

What is claimed is:

1. A retractor assembly for surgery in a patient, comprising:
 a support member;
 a retractor member including a retraction portion defining a first longitudinal axis and extending from said support member between a proximal end and an opposite distal end, said retractor member further including an arm extending along a second axis transverse to the first longitudinal axis from said retraction portion toward said support member; and
 a housing assembly engaged to said support member and to said arm of said retractor member, said housing assembly including:
  a drive mechanism for pivoting said retractor member relative to said support member, said drive mechanism including a rotary member engaged to said arm of said retractor member and a drive member engaged to said rotary member, wherein rotation of said drive member against said rotary member rotates said rotary member about a path defined by a connection of said rotary member to said housing assembly which in turn rotates the arm about the second axis and pivots said distal end of said retraction portion relative to said support member.

2. The retractor assembly of claim 1, wherein:
 said support member is an elongated support member; and
 said housing assembly includes a translation mechanism for linearly moving said retractor member along said elongated support member.

3. The retractor assembly of claim 2, wherein said housing assembly includes a housing body defining a compartment for housing said drive mechanism therein, said housing body including a proximal side defining an opening into said compartment through which said drive member is accessible for operation, wherein a proximal end of said drive member is recessed distally of said proximal side of said housing.

4. The retractor assembly of claim 3, further comprising a locking mechanism mounted to said housing body for releasably locking said housing assembly and said retractor member in position along said support member.

5. The retractor assembly of claim 1, wherein said housing assembly includes a housing body defining:
 a first passage for receiving said elongate member;
 a second passage extending transversely to said first passage for receiving said arm of said retractor member; and
 a compartment that contains said drive mechanism.

6. The retractor assembly of claim 5, wherein said housing assembly includes a biasing member extending between and contacting said rotary member and said housing body, said biasing member forcing said retractor member toward a first orientation relative to said support member, wherein said drive member is operable to move said rotary member against said biasing force to pivot said retraction portion relative to said support member.

7. The retractor assembly of claim 5, wherein said rotary member of said drive mechanism is engaged to said arm of said retractor member in a predetermined and fixed orientation relative to said rotary member, said rotary member further including a mounting part defining a bore for receiving said drive member therein.

8. The retractor assembly of claim 7, wherein said rotary member includes:
 a receiving part defining a bore for removably receiving said arm of said retractor member in said predetermined and fixed orientation relative to said rotary member;
 an internal bore that opens into said bore of said receiving part of said rotary member; and
 a locking mechanism in said internal bore that releasably engages said arm of said retractor member in said bore of said receiving part.

9. The retractor assembly of claim 8, wherein said arm of said retractor includes a mounting feature that receives a locking member of said locking mechanism therein in said locked position.

10. The retractor assembly of claim 9, wherein said arm of said retractor member includes a connection portion having a semi-circular shape with a flat side and said mounting feature is a groove in said flat side, and further wherein said bore of said receiving part includes a semi-circular shape for receiving said connection part of said arm therein.

11. The retractor assembly of claim 7, wherein said drive member includes a body engaged to said bore of said rotary member, said drive member further including a cam-shaped head positioned in contact with an inner surface of said housing body.

12. The retractor assembly of claim 11, wherein said rotary member includes an arced channel extending into said mounting part and said housing assembly includes a control member extending into said arced channel with said control member engaged to said housing body, wherein said rotary member moves around said control member as said drive member is translated to move said rotary member and said control member retains said rotary member in said housing body when said retractor member is disengaged from said rotary member.

13. The retractor assembly of claim 12, wherein said control member and said arced channel extend into said rotary member in a direction paralleling said bore of said receiving part that receives said connection portion of said arm, and said bore of said mounting part extends in a transverse orientation to said bore of said receiving part of said rotary member.

14. The retractor assembly of claim 11, wherein cam-shaped head of said drive member pivots along said inner surface of said housing body as said drive member is rotatingly advanced into said mounting part.

15. A retractor assembly for surgery in a patient, comprising:
 a support member;
 a retractor member including a retraction portion defining a first longitudinal axis and extending transversely to said support member between a proximal end and an opposite distal end, said retractor member further including an arm extending along a second axis transverse to the first longitudinal axis from said retraction portion toward said support member;

a housing assembly engaged to said support member and to said arm of said retractor member, said housing assembly including:
- a housing body extending from said support member and a first passage for receiving said arm of said retractor member in a transverse orientation to said support member; and
- a drive mechanism contained within said housing body for pivoting said retractor member relative to said support member, said drive mechanism including a rotary member engaged to said arm of said retractor member and a drive member engaged to said rotary member, wherein said drive member is accessible through a proximal side of said housing body for application of a driving force thereto that rotates said rotary member along a path that rotates the arm about the second axis and pivots said distal end of said retraction portion relative to said support member from an initial orientation to a pivoted orientation.

16. The retractor assembly of claim 15, wherein said first passage opens at an inner side of said housing body facing said retractor member so that said arm of said retractor member is positioned into said first passage in an endwise orientation.

17. The retractor assembly of claim 16, wherein said rotary member defines a bore for receiving a connection portion of said arm of said retractor member therein, said bore and said connection portion each defining complementary shapes so that said connection portion is received in said bore in a predetermined and fixed orientation of said retractor member relative to said rotary member.

18. The retractor assembly of claim 17, wherein said housing assembly houses a locking mechanism that releasably engages a recess in said connection portion of said arm to secure said retractor member to said housing assembly.

19. The assembly of claim 15, wherein said drive member includes a proximal end oriented toward and recessed distally of said proximal side of said housing body that is accessible to rotate said drive member, said drive member further including an opposite distal end defining a camming surface in contact with an inner surface of said housing body, and rotation of said drive translates said drive member along said rotary member and causes said camming surface to rotate against said inner surface of said housing body as said rotary member rotates to pivot said retractor member.

20. The assembly of claim 19, wherein said drive mechanism includes a biasing member to force said rotary member and said retractor member toward said initial orientation.

21. The assembly of claim 19, wherein said retraction portion is perpendicular to said support member in said initial orientation.

22. The assembly of claim 15, wherein:
- said support member is elongated and extending between a first end and an opposite second end; and
- said housing assembly includes a translation mechanism mounted to said housing body and engaged to said support member for linearly moving said retractor member along said support member.

* * * * *